(12) United States Patent
Digiacomantonio et al.

(10) Patent No.: US 10,596,043 B2
(45) Date of Patent: *Mar. 24, 2020

(54) COLOR PRINTED LAMINATED STRUCTURE, ABSORBENT ARTICLE COMPRISING THE SAME AND PROCESS FOR MANUFACTURING THE SAME

(71) Applicant: The Procter & Gamble Company, Cincinnati, OH (US)

(72) Inventors: Marco Digiacomantonio, Rome (IT); Carlo Toro, Crailsheim (DE); Giovanni Carlucci, Pescara (IT)

(73) Assignee: The Procter & Gamble Company, Cincinnati, OH (US)

(*) Notice: Subject to any disclaimer, the term of this patent is extended or adjusted under 35 U.S.C. 154(b) by 281 days.

This patent is subject to a terminal disclaimer.

(21) Appl. No.: 15/626,386

(22) Filed: Jun. 19, 2017

(65) Prior Publication Data

US 2017/0312140 A1 Nov. 2, 2017

Related U.S. Application Data

(63) Continuation of application No. 14/711,056, filed on May 13, 2015, now Pat. No. 9,707,133, which is a (Continued)

(30) Foreign Application Priority Data

Sep. 19, 2001 (EP) ..................................... 01121751

(51) Int. Cl.
*A61F 13/00* (2006.01)
*A61F 13/15* (2006.01)
(Continued)

(52) U.S. Cl.
CPC .. *A61F 13/15699* (2013.01); *A61F 13/00059* (2013.01); *A61F 13/15577* (2013.01);
(Continued)

(58) Field of Classification Search
CPC .......... A61F 13/00059; A61F 13/15577; A61F 13/15585; A61F 13/15699; A61F 13/511;
(Continued)

(56) References Cited

U.S. PATENT DOCUMENTS

| 3,559,648 A | 2/1971 | Mason, Jr. |
| 3,759,261 A | 9/1973 | Wang |

(Continued)

FOREIGN PATENT DOCUMENTS

| EP | 0299109 | 1/1989 |
| EP | 0503608 | 9/1992 |

(Continued)

OTHER PUBLICATIONS

"Multicolored Absorbent Articles: A Brief History," Jeffrey D. Lindsay and Beth A. Lange, Kimberly-Clark Corporation, Neenah, Wisconsin, Published in: IP.com's Prior Art Database, Oct. 10, 2003; Publication ID: IPCOM000019928D.

(Continued)

*Primary Examiner* — Adam Marcetich
(74) *Attorney, Agent, or Firm* — George H Leal

(57) ABSTRACT

A process for manufacturing a disposable absorbent article is disclosed. The method includes providing a first layer having a first surface and an opposing second surface; color printing the first layer on at least one of the first or second surface; providing a second layer having a first and an opposing second surface; providing a topsheet, an absorbent core, and a backsheet; and placing the first layer and second layer between a topsheet and an absorbent core such that the (Continued)

color printing is visible through a wearer-facing surface of the disposable absorbent article.

29 Claims, 5 Drawing Sheets

Related U.S. Application Data continuation of application No. 13/550,145, filed on Jul. 16, 2012, now Pat. No. 9,050,220, which is a continuation of application No. 10/795,371, filed on Mar. 8, 2004, now abandoned, which is a continuation of application No. PCT/US02/29558, filed on Sep. 18, 2002.

(51) Int. Cl.
| | |
|---|---|
| A61F 13/511 | (2006.01) |
| B32B 5/24 | (2006.01) |
| B32B 5/26 | (2006.01) |
| B41M 1/04 | (2006.01) |
| G03F 7/20 | (2006.01) |
| A61F 13/513 | (2006.01) |
| B32B 5/02 | (2006.01) |
| A61F 13/537 | (2006.01) |
| B41F 5/24 | (2006.01) |

(52) U.S. Cl.
CPC ...... A61F 13/15585 (2013.01); A61F 13/511 (2013.01); A61F 13/5116 (2013.01); A61F 13/51121 (2013.01); A61F 13/51394 (2013.01); A61F 13/53747 (2013.01); B32B 5/022 (2013.01); B32B 5/26 (2013.01); A61F 2013/00153 (2013.01); A61F 2013/15243 (2013.01); A61F 2013/15821 (2013.01); B32B 2262/0253 (2013.01); B32B 2262/0276 (2013.01); B32B 2262/067 (2013.01); B41F 5/24 (2013.01); B41M 1/04 (2013.01); B41P 2200/12 (2013.01); G03F 7/2012 (2013.01); Y10T 428/24802 (2015.01)

(58) Field of Classification Search
CPC ............ A61F 13/51121; A61F 13/5116; A61F 13/51394; A61F 13/53747; A61F 2013/00153; A61F 2013/15243; A61F 2013/15821; B32B 2262/0253; B32B 2262/0276; B32B 2262/067; B32B 5/022; B32B 5/26; B41F 5/24; B41M 1/04; B41P 2200/12; G03F 7/2012; Y10T 428/24802

See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,863,636 A | 2/1975 | Johnson | |
| 3,911,173 A | 10/1975 | Sprague, Jr. | |
| 3,929,135 A | 12/1975 | Thompson | |
| 4,022,211 A | 5/1977 | Timmons et al. | |
| 4,324,246 A | 4/1982 | Mullane et al. | |
| 4,342,314 A | 8/1982 | Radel et al. | |
| 4,381,781 A | 5/1983 | Sciaraffa et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman | |
| 4,629,643 A | 12/1986 | Curro | |
| 4,636,207 A | 1/1987 | Buell | |
| 4,648,876 A | 3/1987 | Becker et al. | |
| 4,662,875 A | 5/1987 | Hirotsu et al. | |
| 4,673,402 A | 6/1987 | Weisman et al. | |
| 4,673,403 A | 6/1987 | Lassen et al. | |
| 4,695,278 A | 9/1987 | Lawson | |
| 4,699,622 A | 10/1987 | Toussant et al. | |
| 4,704,115 A | 11/1987 | Buell | |
| 4,710,189 A | 12/1987 | Lash | |
| 4,758,241 A | 7/1988 | Lassen et al. | |
| 4,785,996 A | 11/1988 | Ziecker et al. | |
| 4,795,454 A | 1/1989 | Dragoo | |
| 4,808,178 A | 2/1989 | Aziz et al. | |
| 4,816,025 A | 3/1989 | Foreman | |
| 4,834,735 A | 5/1989 | Alemany et al. | |
| 4,842,666 A | 6/1989 | Werenicz | |
| 4,857,067 A | 8/1989 | Wood et al. | |
| 4,846,815 A | 11/1989 | Scripps et al. | |
| 4,888,231 A | 12/1989 | Angstadt | |
| 4,892,536 A | 1/1990 | DesMarais et al. | |
| 4,894,060 A | 1/1990 | Nestegard | |
| 4,900,317 A | 2/1990 | Buell | |
| 4,909,803 A | 3/1990 | Aziz et al. | |
| 4,938,753 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,988,344 A | 1/1991 | Reising et al. | |
| 4,990,147 A | 2/1991 | Freeland | |
| 5,006,394 A | 4/1991 | Baird | |
| 5,026,364 A | 6/1991 | Robertson | |
| 5,035,691 A | 7/1991 | Zimmel et al. | |
| 5,036,978 A | 8/1991 | Frank et al. | |
| 5,037,416 A | 8/1991 | Allen et al. | |
| 5,050,742 A | 9/1991 | Muckenfuhs | |
| 5,054,619 A | 10/1991 | Muckenfuhs | |
| 5,062,840 A | 11/1991 | Holt et al. | |
| 5,085,654 A | 2/1992 | Buell | |
| 5,098,422 A | 3/1992 | Davis et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Drier et al. | |
| 5,221,274 A | 6/1993 | Buell et al. | |
| 5,221,275 A | 6/1993 | Van Iten | |
| 5,226,538 A | 7/1993 | Roselle | |
| 5,242,436 A | 9/1993 | Weil et al. | |
| D340,978 S | 11/1993 | Atcheson et al. | |
| 5,260,345 A | 11/1993 | DesMarais et al. | |
| 5,269,755 A | 12/1993 | Bodicky | |
| 5,269,775 A | 12/1993 | Freeland et al. | |
| 5,280,345 A | 1/1994 | Uehara et al. | |
| 5,300,054 A | 4/1994 | Feist et al. | |
| 5,304,161 A | 4/1994 | Noel et al. | |
| 5,306,266 A | 4/1994 | Freeland | |
| 5,342,338 A | 8/1994 | Roe | |
| 5,342,861 A | 8/1994 | Raykovitz | |
| H1376 H | 11/1994 | Osborn et al. | |
| 5,387,207 A | 2/1995 | Dyer et al. | |
| 5,397,318 A | 3/1995 | Dreier | |
| 5,399,174 A * | 3/1995 | Yeo .................. | D04H 3/12 604/365 |
| 5,401,267 A | 3/1995 | Couture-Dorschner et al. | |
| RE34,920 E | 4/1995 | Aziz et al. | |
| 5,415,650 A | 5/1995 | Sigl | |
| 5,439,458 A | 8/1995 | Noel et al. | |
| 5,458,590 A | 10/1995 | Schleinz | |
| 5,492,751 A | 2/1996 | Butt, Sr. et al. | |
| 5,499,978 A | 3/1996 | Buell et al. | |
| 5,503,076 A | 4/1996 | Yeo | |
| 5,507,736 A | 4/1996 | Clear et al. | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,554,145 A | 9/1996 | Roe et al. | |
| D374,928 S | 10/1996 | Murji et al. | |
| 5,569,234 A | 10/1996 | Buell et al. | |
| 5,571,096 A | 11/1996 | Dobrin et al. | |

(56) References Cited

U.S. PATENT DOCUMENTS

| | | |
|---|---|---|
| 5,580,411 A | 12/1996 | Nease et al. |
| H1630 H | 1/1997 | Roe |
| 5,591,152 A | 1/1997 | Buell et al. |
| 5,607,760 A | 3/1997 | Roe |
| 5,609,587 A | 3/1997 | Roe |
| 5,614,230 A | 3/1997 | Weyenberg et al. |
| 5,625,222 A | 4/1997 | Yoneda et al. |
| 5,635,191 A | 6/1997 | Roe |
| H1670 H | 7/1997 | Aziz et al. |
| 5,643,588 A | 7/1997 | Roe et al. |
| 5,653,703 A | 8/1997 | Roe et al. |
| 5,658,269 A | 8/1997 | Osborn, III |
| 5,660,928 A | 8/1997 | Stokes et al. |
| 5,669,897 A | 9/1997 | LaVon et al. |
| 5,674,590 A | 10/1997 | Anderson et al. |
| 5,683,358 A | 11/1997 | Nielsen et al. |
| D387,158 S | 12/1997 | Unger et al. |
| 5,716,900 A | 2/1998 | Kronzer et al. |
| 5,766,212 A | 6/1998 | Jitoe et al. |
| 5,766,389 A | 6/1998 | Brandon et al. |
| 5,818,719 A | 10/1998 | Brandon et al. |
| 5,829,076 A | 11/1998 | Csikos et al. |
| 5,853,859 A | 12/1998 | Levy et al. |
| 5,865,823 A | 2/1999 | Curro |
| 5,866,242 A | 2/1999 | Tan et al. |
| 5,885,418 A | 3/1999 | Anderson et al. |
| 5,891,120 A | 4/1999 | Chmielewski |
| 5,897,541 A | 4/1999 | Uitenbroek |
| 5,904,971 A | 5/1999 | Anderson et al. |
| 5,925,712 A | 7/1999 | Kronzer et al. |
| 5,930,139 A | 7/1999 | Chapdelaine et al. |
| D412,574 S | 8/1999 | Trombetta et al. |
| 5,932,039 A | 8/1999 | Popp et al. |
| 5,934,470 A | 8/1999 | Bauer et al. |
| 5,949,444 A | 9/1999 | Geserich et al. |
| 5,962,149 A | 10/1999 | Kronzer et al. |
| 5,964,970 A | 10/1999 | Woolwine et al. |
| 5,980,087 A | 11/1999 | Brandon et al. |
| 6,004,306 A | 12/1999 | Robles et al. |
| 6,010,490 A | 1/2000 | Freeland et al. |
| 6,033,502 A | 3/2000 | Coenen et al. |
| 6,033,739 A | 3/2000 | Kronzer et al. |
| D423,098 S | 4/2000 | Stancyk |
| 6,077,255 A | 6/2000 | Hunter et al. |
| 6,079,326 A | 6/2000 | Strutz et al. |
| 6,082,256 A | 7/2000 | Hellmeier et al. |
| 6,092,002 A | 7/2000 | Kastman et al. |
| 6,103,364 A | 8/2000 | Harris et al. |
| 6,114,597 A | 9/2000 | Romare et al. |
| 6,168,584 B1 | 1/2001 | Allen et al. |
| 6,221,211 B1 * | 4/2001 | Hollenberg ............ B32B 29/00 162/123 |
| 6,234,742 B1 | 5/2001 | Rodefeld et al. |
| 6,245,051 B1 | 6/2001 | Zenker et al. |
| 6,245,168 B1 | 6/2001 | Coenen et al. |
| 6,257,136 B1 | 7/2001 | McCoy et al. |
| 6,264,640 B1 | 7/2001 | Sutton |
| 6,265,053 B1 | 7/2001 | Kronzer et al. |
| 6,296,339 B1 | 10/2001 | Geserich et al. |
| 6,297,424 B1 | 10/2001 | Olson et al. |
| 6,307,119 B1 | 10/2001 | Cammarota et al. |
| 6,350,257 B1 | 2/2002 | Bjorklund et al. |
| 6,354,984 B1 | 3/2002 | Hensley et al. |
| 6,379,813 B1 | 4/2002 | Anderson et al. |
| 6,429,351 B1 | 8/2002 | Guidotti et al. |
| 6,432,098 B1 | 8/2002 | Kline et al. |
| 6,454,095 B1 | 9/2002 | Brisebois et al. |
| 6,476,288 B1 | 11/2002 | Van Rijswijck et al. |
| 6,482,192 B2 | 11/2002 | Haarer et al. |
| 6,492,574 B1 | 12/2002 | Chen Fung-Jou et al. |
| 6,495,229 B1 | 12/2002 | Carte et al. |
| 6,497,690 B2 | 12/2002 | Haarer et al. |
| 6,503,977 B1 | 1/2003 | Branham et al. |
| 6,531,204 B2 | 3/2003 | Suekane et al. |
| 6,551,431 B2 | 4/2003 | Lee |
| 6,558,499 B1 | 5/2003 | Pargass et al. |
| 6,568,530 B2 | 5/2003 | Takahashi et al. |
| 6,572,575 B1 | 6/2003 | Shimada et al. |
| 6,572,602 B2 | 6/2003 | Furuya et al. |
| 6,586,653 B2 | 7/2003 | Graeme et al. |
| 6,595,042 B2 | 7/2003 | Holliday et al. |
| 6,596,918 B2 | 7/2003 | Wehrle et al. |
| 6,601,705 B2 | 8/2003 | Molina et al. |
| 6,617,488 B1 | 9/2003 | Springer et al. |
| 6,624,100 B1 | 9/2003 | Pike |
| 6,647,878 B2 | 11/2003 | Blau et al. |
| 6,651,551 B1 | 11/2003 | Castellanos |
| 6,671,936 B1 * | 1/2004 | Carlson ................... B32B 5/26 28/104 |
| 6,673,204 B2 | 1/2004 | Takai et al. |
| 6,676,625 B2 | 1/2004 | Bernard |
| 6,681,934 B2 | 1/2004 | Kolterjohn et al. |
| 6,685,020 B2 | 2/2004 | Brisebois et al. |
| 6,699,227 B2 | 3/2004 | Haarer et al. |
| 6,703,086 B2 | 3/2004 | Kronzer et al. |
| 6,710,221 B1 | 3/2004 | Pierce et al. |
| 6,732,778 B1 | 5/2004 | Machida et al. |
| 6,733,483 B2 | 5/2004 | Raufman et al. |
| 6,733,865 B2 | 5/2004 | Taniguchi et al. |
| 6,747,185 B2 | 6/2004 | Inoue et al. |
| 6,763,944 B2 | 7/2004 | Ronn et al. |
| 6,788,803 B2 | 9/2004 | Calvert et al. |
| 6,797,858 B2 | 9/2004 | Erdman et al. |
| 6,827,806 B2 | 12/2004 | Uitenbroek |
| 6,837,958 B2 | 1/2005 | Otsubo et al. |
| 6,911,106 B2 | 6/2005 | Otsubo et al. |
| 6,921,647 B2 | 7/2005 | Kritzman et al. |
| 6,932,798 B2 | 8/2005 | Kudo et al. |
| 6,946,585 B2 | 9/2005 | London Brown |
| 6,949,681 B2 | 9/2005 | Linsell |
| 6,949,689 B2 | 9/2005 | Noda et al. |
| 6,953,602 B2 | 10/2005 | Carte et al. |
| 6,957,884 B2 | 10/2005 | Sharma et al. |
| 6,962,110 B2 | 11/2005 | Hellmeier et al. |
| 6,984,770 B2 | 1/2006 | Graeme et al. |
| 7,030,176 B2 | 4/2006 | Nohr et al. |
| 7,034,199 B2 | 4/2006 | Suekane et al. |
| 7,153,385 B2 | 12/2006 | Andersson et al. |
| 7,153,561 B2 | 12/2006 | Larson et al. |
| 7,159,532 B2 | 1/2007 | Klofta et al. |
| 7,169,137 B2 | 1/2007 | Shimada et al. |
| 7,172,667 B2 | 2/2007 | Vergona et al. |
| 7,178,571 B2 | 2/2007 | Vergona et al. |
| 7,185,761 B2 | 3/2007 | Klofta et al. |
| 7,214,849 B2 | 5/2007 | Sakaguchi et al. |
| 7,226,438 B2 | 6/2007 | Soga et al. |
| 7,322,472 B2 | 1/2008 | Swiecicki et al. |
| 7,371,456 B2 | 5/2008 | Nohr et al. |
| 7,394,391 B2 | 7/2008 | Long et al. |
| 7,432,412 B2 | 10/2008 | Kigata et al. |
| 7,477,156 B2 | 1/2009 | Long et al. |
| 7,511,186 B2 | 3/2009 | Kikuchi et al. |
| 7,511,187 B2 | 3/2009 | Kelly et al. |
| 7,520,873 B2 | 4/2009 | Swiecicki et al. |
| 7,530,972 B2 | 5/2009 | Ando et al. |
| 7,531,055 B2 | 5/2009 | Mead et al. |
| 7,540,236 B2 | 6/2009 | Aichele et al. |
| 7,604,425 B2 | 10/2009 | Otsuka et al. |
| 7,626,072 B2 | 12/2009 | Mocadio |
| 7,632,257 B2 | 12/2009 | Magee et al. |
| 7,704,589 B2 | 4/2010 | Olson et al. |
| 7,765,614 B2 | 8/2010 | Takino et al. |
| 7,786,340 B2 | 8/2010 | Gagliardi et al. |
| 7,812,214 B2 | 10/2010 | Koele et al. |
| 7,833,209 B2 | 11/2010 | Noda et al. |
| 7,851,666 B2 | 12/2010 | Belau et al. |
| 7,867,208 B2 | 1/2011 | Samuelsson et al. |
| 7,919,668 B2 | 4/2011 | Belau et al. |
| 7,931,638 B2 | 4/2011 | Yao et al. |
| 7,956,234 B2 | 6/2011 | Sosalla et al. |
| 7,956,754 B2 | 6/2011 | Long et al. |
| 7,959,620 B2 | 6/2011 | Miura et al. |
| 7,992,994 B2 | 8/2011 | Kobayashi et al. |
| 8,003,846 B2 | 8/2011 | Stranemalm et al. |

(56) References Cited

U.S. PATENT DOCUMENTS

| | | |
|---|---|---|
| 8,016,934 B2 | 9/2011 | Misaki et al. |
| 8,016,978 B2 | 9/2011 | Sauter et al. |
| 8,057,451 B2 | 11/2011 | Otsubo et al. |
| 8,084,516 B2 | 12/2011 | Takemura et al. |
| 8,153,163 B2 | 4/2012 | Misaki et al. |
| 8,197,455 B2 | 6/2012 | Zander et al. |
| 8,236,385 B2 | 6/2012 | Stangenes et al. |
| 8,256,854 B2 | 9/2012 | Till et al. |
| 8,264,732 B2 | 9/2012 | Anderson et al. |
| 8,268,103 B2 | 9/2012 | Till et al. |
| 8,273,066 B2 | 9/2012 | Anderson et al. |
| 8,304,597 B2 | 11/2012 | Hughes et al. |
| 8,309,789 B2 | 11/2012 | Stenberg et al. |
| 8,349,117 B2 | 1/2013 | Otsubo et al. |
| 8,372,053 B2 | 2/2013 | Shimada et al. |
| 8,377,022 B2 | 2/2013 | Noda et al. |
| 8,378,165 B2 | 2/2013 | Visccher et al. |
| 8,387,530 B2 | 3/2013 | Larson et al. |
| 8,435,625 B2 | 5/2013 | Ruehe et al. |
| 8,449,517 B2 | 5/2013 | Ueda et al. |
| 8,479,920 B2 | 7/2013 | Biber et al. |
| 8,486,036 B2 | 7/2013 | Tange et al. |
| 8,518,009 B2 | 8/2013 | Saito et al. |
| 8,529,725 B2 | 9/2013 | Bishop et al. |
| 8,545,678 B2 | 10/2013 | Sauter et al. |
| 8,557,894 B2 | 10/2013 | Gil et al. |
| 8,603,061 B2 | 12/2013 | Yao et al. |
| 2001/0002605 A | 1/2001 | Morawski et al. |
| 2001/0004688 A1 | 6/2001 | Lee |
| 2001/0031954 A1 | 10/2001 | Jordan et al. |
| 2001/0044249 A1* | 11/2001 | Demott .................. A47G 23/03 442/304 |
| 2001/0056270 A1 | 12/2001 | Mizutani et al. |
| 2002/0007162 A1 | 1/2002 | Cammarota et al. |
| 2002/0025752 A1 | 2/2002 | Taniguchi et al. |
| 2002/0049418 A1 | 4/2002 | London Brown |
| 2002/0143309 A1 | 10/2002 | Glasgow et al. |
| 2002/0143312 A1* | 10/2002 | Graeme, III .......... A61F 13/511 604/385.01 |
| 2002/0146534 A1* | 10/2002 | Kaufman ............. A47G 11/003 428/88 |
| 2002/0017322 A1 | 12/2002 | Molee |
| 2002/0187322 A1 | 12/2002 | Molee |
| 2003/0011481 A1 | 1/2003 | Bjorkman et al. |
| 2003/0028162 A1 | 2/2003 | Haarer et al. |
| 2003/0028987 A1 | 2/2003 | Morakawshi et al. |
| 2003/0065299 A1 | 4/2003 | Carlucci et al. |
| 2003/0065300 A1 | 4/2003 | Suga et al. |
| 2003/0073966 A1 | 4/2003 | Sosalla et al. |
| 2003/0078553 A1 | 4/2003 | Wada Mitsuhiro et al. |
| 2003/0091796 A1 | 5/2003 | Suekane et al. |
| 2003/0106825 A1 | 6/2003 | Wada Mitsuhiro et al. |
| 2003/0109839 A1 | 6/2003 | Costea et al. |
| 2003/0114809 A1 | 6/2003 | Gagliardi et al. |
| 2003/0114818 A1 | 6/2003 | Benecke |
| 2003/0114848 A1 | 6/2003 | Cobb |
| 2003/0130632 A1 | 7/2003 | Costea et al. |
| 2003/0158532 A1 | 8/2003 | Magee et al. |
| 2003/0187415 A1 | 10/2003 | Kudo et al. |
| 2004/0023006 A1 | 2/2004 | Mead et al. |
| 2004/0050738 A1 | 3/2004 | Molina et al. |
| 2004/0102748 A1 | 5/2004 | Hirotsu |
| 2004/0118530 A1 | 6/2004 | Kressner et al. |
| 2004/0121675 A1 | 6/2004 | Snowden et al. |
| 2004/0122386 A1 | 6/2004 | Mocadlo |
| 2004/0211329 A1 | 10/2004 | Funahata et al. |
| 2004/0265544 A1 | 12/2004 | Di Salvo et al. |
| 2004/0267217 A1 | 12/2004 | Bhupendra et al. |
| 2004/0267226 A1 | 12/2004 | Dabi et al. |
| 2005/0008830 A1 | 1/2005 | Larson et al. |
| 2005/0027278 A1 | 2/2005 | Mizutani et al. |
| 2005/0065489 A1 | 3/2005 | Driskell et al. |
| 2005/0096614 A1 | 5/2005 | Perez et al. |
| 2005/0096616 A1 | 5/2005 | Arora et al. |
| 2005/0165373 A1 | 7/2005 | Brown et al. |
| 2005/0197641 A1 | 9/2005 | Rajagopalan |
| 2005/0209576 A1 | 9/2005 | Hirotsu |
| 2005/0217791 A1 | 10/2005 | Costello et al. |
| 2005/0227048 A1 | 10/2005 | Junior et al. |
| 2006/0003657 A1 | 1/2006 | Larson et al. |
| 2006/0011316 A1 | 1/2006 | Kressner et al. |
| 2006/0020251 A1 | 1/2006 | Kelly et al. |
| 2006/0025736 A1 | 2/2006 | Berg et al. |
| 2006/0025743 A1 | 2/2006 | Hasse et al. |
| 2006/0111684 A1 | 5/2006 | Berba et al. |
| 2006/0129115 A1 | 6/2006 | Visccher et al. |
| 2006/0129116 A1 | 6/2006 | Hughes et al. |
| 2006/0135936 A1 | 6/2006 | Markovich et al. |
| 2006/0148932 A1 | 7/2006 | Nohr et al. |
| 2006/0173428 A1 | 8/2006 | Acors et al. |
| 2006/0173429 A1 | 8/2006 | Acors et al. |
| 2006/0188551 A1 | 8/2006 | Hauser et al. |
| 2007/0003736 A1 | 1/2007 | Saarvali et al. |
| 2007/0043331 A1 | 2/2007 | Haruki et al. |
| 2007/0100308 A1 | 5/2007 | Miyairi et al. |
| 2007/0100309 A1 | 5/2007 | Uda et al. |
| 2007/0282287 A1 | 5/2007 | Noda et al. |
| 2007/0276348 A1 | 11/2007 | Stenberg et al. |
| 2008/0038537 A1 | 2/2008 | Yano et al. |
| 2008/0152810 A1 | 6/2008 | Nohr et al. |
| 2008/0221543 A1 | 9/2008 | Wilkes et al. |
| 2008/0227356 A1 | 9/2008 | Poruthoor et al. |
| 2008/0234643 A1 | 9/2008 | Kaneda et al. |
| 2008/0263975 A1 | 10/2008 | Mead et al. |
| 2008/0314266 A1 | 12/2008 | Reinholdt et al. |
| 2009/0035515 A1 | 2/2009 | Cecconi et al. |
| 2009/0157021 A1 | 6/2009 | Sullivan et al. |
| 2009/0169745 A1 | 7/2009 | Nohr et al. |
| 2009/0171307 A1 | 7/2009 | Chang et al. |
| 2009/0240221 A1 | 9/2009 | Rothenberger et al. |
| 2009/0247979 A1 | 10/2009 | Sosalla et al. |
| 2009/0321220 A1 | 12/2009 | Ewerlof et al. |
| 2010/0030173 A1 | 2/2010 | Song et al. |
| 2010/0100067 A1 | 4/2010 | Pugliese, III et al. |
| 2010/0129620 A1 | 5/2010 | Lopez-Mas et al. |
| 2010/0272965 A1 | 10/2010 | Schinkoreit et al. |
| 2010/0298800 A1 | 11/2010 | Berg et al. |
| 2011/0009843 A1 | 1/2011 | Krook et al. |
| 2011/0015063 A1 | 1/2011 | Gil et al. |
| 2011/0015597 A1 | 1/2011 | Gil et al. |
| 2011/0015599 A1 | 1/2011 | Song et al. |
| 2011/0028929 A1 | 2/2011 | Hopkins et al. |
| 2011/0077609 A1 | 3/2011 | Kuwano et al. |
| 2011/0088828 A1 | 4/2011 | Skabroud et al. |
| 2011/0144610 A1 | 6/2011 | Karlson et al. |
| 2011/0146900 A1 | 6/2011 | Ruman et al. |
| 2011/0172626 A1 | 7/2011 | Mitsuno et al. |
| 2011/0179959 A1 | 7/2011 | Gerigk et al. |
| 2011/0213325 A1 | 9/2011 | Gabrielii et al. |
| 2011/0313388 A1 | 12/2011 | Gabrielii et al. |
| 2012/0010581 A1 | 1/2012 | Mason et al. |
| 2012/0022411 A1 | 1/2012 | Wu et al. |
| 2012/0035563 A1 | 2/2012 | Ruman et al. |
| 2012/0035568 A1 | 2/2012 | Nelson et al. |
| 2012/0143160 A1 | 6/2012 | Song et al. |
| 2012/0150134 A1 | 6/2012 | Wei et al. |
| 2012/0165771 A1 | 6/2012 | Ruman et al. |
| 2012/0173249 A1 | 7/2012 | Popp et al. |
| 2012/0177886 A1 | 7/2012 | Kanya et al. |
| 2012/0179125 A1 | 7/2012 | Kanya et al. |
| 2012/0179126 A1 | 7/2012 | Kanya et al. |
| 2012/0189814 A1 | 7/2012 | Coslett et al. |
| 2012/0232511 A1 | 9/2012 | Velazquez et al. |
| 2012/0232515 A1 | 9/2012 | Suga et al. |
| 2012/0253306 A1 | 10/2012 | Otsubo et al. |
| 2012/0253308 A1 | 10/2012 | Misiti et al. |
| 2012/0283682 A1 | 11/2012 | Otsubo et al. |
| 2012/0328850 A1 | 12/2012 | Yahiaoui et al. |
| 2012/0330258 A1 | 12/2012 | Poruthoor et al. |
| 2013/0178811 A1 | 7/2013 | Kikuchi et al. |
| 2013/0190710 A1 | 7/2013 | Yoshioka et al. |
| 2013/0211361 A1 | 8/2013 | Anderson et al. |
| 2013/0248398 A1 | 9/2013 | Harada et al. |
| 2013/0310784 A1 | 11/2013 | Bryant et al. |

(56) References Cited

U.S. PATENT DOCUMENTS

FOREIGN PATENT DOCUMENTS

| | | |
|---|---|---|
| EP | 0934737 | 8/1999 |
| EP | 1147755 | 10/2001 |
| EP | 1174104 | 1/2002 |
| EP | 1179329 | 2/2002 |
| EP | 1208823 | 5/2002 |
| EP | 1327427 | 7/2003 |
| JP | 2002-360620 | 12/2002 |
| JP | 2003-52743 | 2/2003 |
| JP | 2003-175076 | 6/2003 |
| JP | 2003-230592 | 8/2003 |
| WO | WO95016746 | 6/1995 |
| WO | WO00076439 | 12/2000 |
| WO | WO00149230 | 7/2001 |
| WO | WO01072252 | 10/2001 |
| WO | WO00236177 | 5/2002 |
| WO | WO02096331 | 12/2002 |
| WO | WO03007997 | 1/2003 |
| WO | WO03013406 | 2/2003 |
| WO | WO03032884 | 4/2003 |
| WO | WO03070136 | 8/2003 |
| WO | WO03070139 | 8/2003 |
| WO | WO2004006818 | 1/2004 |
| WO | WO2004026203 | 4/2004 |
| WO | WO9620682 | 7/2011 |

OTHER PUBLICATIONS

All Office Actions, U.S. Appl. No. 10/902,819, filed Jul. 30, 2004.
All Office Actions, U.S. Appl. No. 10/902,820, filed Jul. 30, 2004.
All Office Actions, U.S. Appl. No. 10/903,221, filed Jul. 30, 2004.
All Office Actions, U.S. Appl. No. 11/012,997, filed Dec. 15, 2004.
All Office Actions, U.S. Appl. No. 11/012,834, filed Dec. 15, 2014.
All Office Actions, U.S. Appl. No. 11/013,268, filed Dec. 15, 2004.
All Office Actions, U.S. Appl. No. 10/795,371, filed Mar. 8, 2004.
All Office Actions, U.S. Appl. No. 12/848,344, filed Aug. 2, 2010.
All Office Actions, U.S. Appl. No. 14/541,747, filed Nov. 14, 2014.
All Office Actions, U.S. Appl. No. 13/741,757, filed Jan. 15, 2013.
All Office Actions, U.S. Appl. No. 13/234,188, filed Sep. 16, 2011.
All Office Actions, U.S. Appl. No. 13/759,165, filed Feb. 5, 2013.
All Office Actions, U.S. Appl. No. 13/550,145, filed Jul. 16, 2012.
All Office Actions, U.S. Appl. No. 13/668,789, filed Nov. 5, 2012.
All Office Actions, U.S. Appl. No. 14/276,183, filed May 13, 2014.
All Office Actions, U.S. Appl. No. 14/711,056, filed May 13, 2015.

\* cited by examiner

COLOR PRINTED LAMINATED STRUCTURE, ABSORBENT ARTICLE COMPRISING THE SAME AND PROCESS FOR MANUFACTURING THE SAME

FIELD OF THE INVENTION

The present invention relates to a liquid permeable color printed laminated structure comprising at least a first and a second layer, the second layer being a fibrous web, preferably a dry laid fibrous web, the first layer being color printed on one of its surface before applying thereto fibers to form the fibrous web and stabilizing the resulting laminated structure. The present invention also relates to a process for manufacturing such a color printed laminated structure and to disposable absorbent articles comprising such a color printed laminated structure typically as a so-called secondary topsheet directly underlying the primary topsheet of the articles.

BACKGROUND OF THE INVENTION

Conventional absorbent articles normally comprise a liquid permeable (pervious) topsheet having a user-facing surface, a liquid impermeable (impervious) backsheet having a garment-facing surface and an absorbent core located intermediate the topsheet and the backsheet.

These elements of absorbent articles like feminine protection articles namely sanitary napkins and/or panty liners, are typically provided in white color, thereby providing a hygienic condition. Upon body fluid discharge like menstruation the absorbent article, typically the absorbent core, absorbs colored body fluid, and changes color to that of the fluid being absorbed. This is distasteful to the user. It is, therefore extremely desirable to provide a clean appearance and a dry surface after the discharge of colored body fluids thereon.

Also each menstrual period is very troublesome for women and almost all the women are in a depressed mood during menstruation. It has been found that there is thus a need for an absorbent article for feminine protection with which a woman may be relieved from a melancholic mood and may experience menstruation without distress or inconvenience.

This problem could be addressed per absorbent articles with a color printed non-woven as the topsheet. Although in the field of absorbent articles for baby protection it is known to color print non-woven (especially the backsheet of diapers), the use of this technology in absorbent articles for feminine protection as a topsheet directly facing the wearer's skin still encounters negatives like color bleeding and/or color rub-off towards the wearer's skin, this especially under wet conditions per discharge of body fluids on the articles.

Furthermore the use of color printing technology on for example body fluid receiving/transmitting elements/layers of absorbent articles should not jeopardize the primary benefits of said elements/layers and hence of the overall body fluid handling properties of the articles per se.

It is thus an object of the present invention to provide an absorbent article for feminine protection which provides a pleasant feeling to a woman before she uses it and which is so structured as to be disposed off cleanly while concealing the flow once the article is used.

It is a further object of the present invention to provide improved colored printed elements/layers for use in absorbent articles for feminine protection typically as topsheet (preferably as secondary topsheet) with reduced color bleeding and reduced color rub-off without compromising on the inherent acquisition, diffusion/transmission and absorption properties of such elements/layers.

It has now been found that these objects are solved by providing a color printed liquid permeable laminated structure comprising at least a first layer and a second layer, each layer having a first outer surface and a second outer surface, the two surfaces being opposite each other, the first layer being color printed on at least one of its surfaces (i.e., at least on its first or second surface or both) prior being laminated to the second layer, the second layer being a fibrous web, preferably a dry laid fibrous web, the laminated structure being stabilized by a bonding means preferably a latex binder, and a process for manufacturing such a laminated structure.

Advantageously by color printing the first layer, preferably a non-woven, prior laminating it to fibers to form a fibrous (dry-laid) web and stabilizing the resulting laminated structure per bonding means, preferably latex binder, the laminated structure retains essentially all its acquisition, diffusion and absorption properties towards body fluid deposited thereon. In contrast, color printing as a subsequent step, a laminated structure after having laminated a first layer, e.g., a nonwoven, to a (dry laid) fibrous web and stabilized the resulting structure per bonding means, results in lost of acquisition, diffusion and absorption properties of the laminated structure. Indeed, printing with conventional printing technologies known to those skilled in the art (e.g., flexography) one surface of such a laminated structure (once laminated) results in caliper reduction of the whole laminated structure thickness, thereby increasing the density of the fibrous dry laid web, and hence reducing its body fluid handling properties.

Advantageously stabilizing the color printed laminated structure of the present invention by applying a bonding means preferably a latex binder contributes to reduced color bleeding and reduced color rub-off.

In a broadest aspect the present invention also encompasses an absorbent article for feminine protection comprising a liquid permeable topsheet, an underlying layer directly adjacent to the topsheet and visible through the liquid permeable topsheet, a liquid impermeable backsheet and an absorbent core positioned between the underlying layer and the backsheet, the underlying layer visible through the topsheet is a color printed liquid permeable laminated structure comprising at least two liquid permeable layers, each layer having a pair of opposed surfaces, at least one of said layers of the laminated structure is color printed on at least the surface directly adjacent another liquid permeable layer of the laminated structure, prior laminating the liquid permeable layers of the laminated structure together. Advantageously such construction results in reduced color bleeding and reduced color rub-off towards the topsheet while not compromising on the body fluid handling properties of the article.

BACKGROUND ART OF THE INVENTION

Ink-printed non-woven fibrous webs and absorbent articles comprising the same are known in the art.

Representative of the art are the following references:

U.S. Pat. No. 5,458,590 discloses ink-printed non-woven fibrous web comprising a non-woven fibrous web comprising a pair of opposed surfaces, and an image printed with an ink on one of said surfaces, said non-woven fibrous web having an average wet crockfastness value of at least about 4 or greater. '590 also discloses disposable absorbent articles comprising a topsheet, a backsheet and an absorbent composite, the backsheet comprising such a ink-printed nonwoven fibrous web.

EP-A-934 737 discloses an absorbent article comprising a topsheet, a backsheet and an absorbent core intermediate the topsheet and the backsheet. The topsheet includes a primary topsheet and a secondary topsheet. At least some of the primary topsheet has apertures arranged in a regularly spaced first pattern. At least some of the secondary topsheet has indicia arranged in a regularly spaced second pattern, the indicia being positioned, shaped and dimensioned to be substantially homogeneously visible through the apertures in a first or non-position, the secondary topsheet being pivoted relative to the primary topsheet by a pivot angle from the first position to a second or in-use position so that the indicia of the secondary topsheet are differentially out of alignment with the apertures of the primary topsheet, forming a regularly spaced third pattern. The regularly spaced third pattern facilitates correct positioning of the absorbent article whilst, simultaneously, masking any colored fluid absorbed by the absorbent core.

None of these prior art discloses, nor teaches the color printed laminated structures as presently claimed, nor absorbent articles comprising the same, let alone a process for manufacturing the same.

SUMMARY OF THE INVENTION

The present invention relates to a color printed liquid permeable laminated structure comprising at least a first liquid permeable layer and a second liquid permeable fibrous layer and their incorporation into disposable absorbent articles. In some embodiments, a process for manufacturing a disposable absorbent article comprises the steps of: providing a first nonwoven layer comprising first constituent fibers, wherein the first constituent fibers comprise bi-component fibers, and wherein the first nonwoven layer has a first surface and an opposing second surface; color printing the first nonwoven layer on at least one of the first surface or second surface, wherein the color printing comprises more than one color; providing a second nonwoven layer comprising second constituent fibers, wherein the second constituent fibers comprise bi-component fibers, and wherein the second nonwoven layer has a first surface and an opposing second surface; joining the first nonwoven layer and the second nonwoven layer together to form a laminate structure, wherein the color printing is disposed on the surface which faces the second nonwoven layer; providing a topsheet, an absorbent core, and a backsheet; and placing the laminate between a topsheet and an absorbent core such that the color printing is visible through the topsheet.

In another embodiment, a process for manufacturing a disposable absorbent article comprising the steps of: providing a first nonwoven layer comprising first constituent fibers, and wherein the first nonwoven layer has a first surface and an opposing second surface; adding pigment to the first constituent fibers; color printing the first nonwoven layer on at least one of the first surface or second surface; providing a second nonwoven layer comprising second constituent fibers, and wherein the second nonwoven layer has a first surface and an opposing second surface; joining the first nonwoven layer and the second nonwoven layer together to form a laminate structure, wherein the color printing is disposed on the surface which faces the second nonwoven layer; providing an absorbent core, and a backsheet; and utilizing the laminate as a topsheet.

BRIEF DESCRIPTION OF THE DRAWINGS

While the specification concludes with claims particularly pointing out and distinctly claiming the present invention, it is believed that the present invention will be better understood from the following description in conjunction with the following drawings:

DETAILED DESCRIPTION OF THE INVENTION

Definitions

Figure 1:
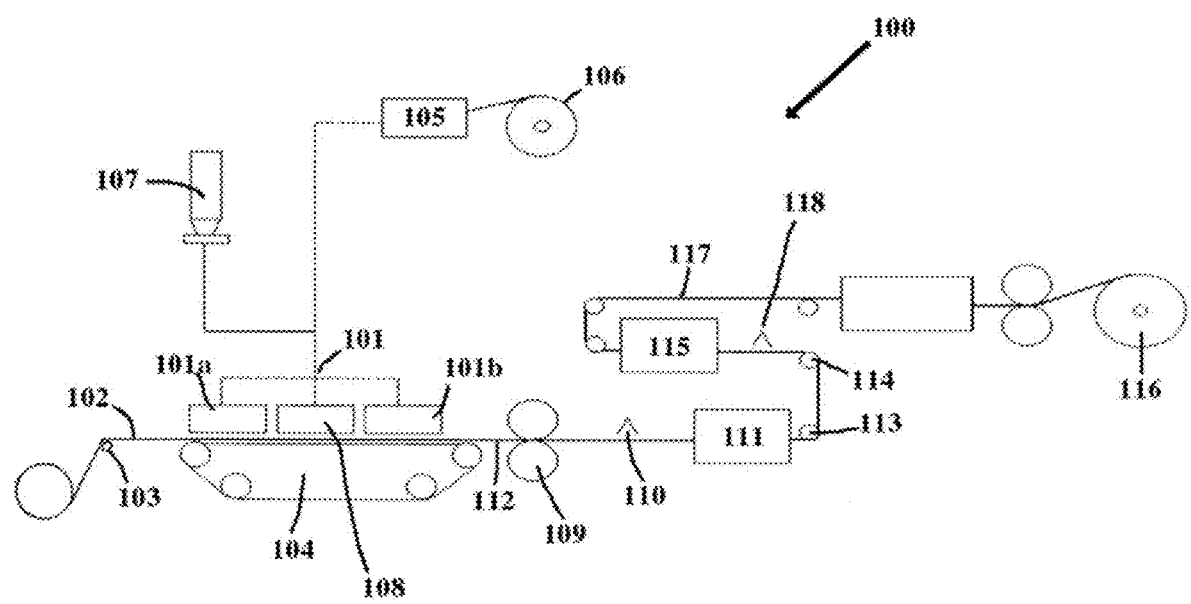
FIG. 1 is a schematic, fragmentary side elevational view of an apparatus for making a laminated structure according to the present invention.

The term "absorbent article" as used herein embraces articles, which absorb and contain body exudates. More specifically, the term relates to articles placed against or in proximity to the body of a user to absorb and contain the various exudates discharged from the user's body. The term "absorbent article" is intended to include baby diapers, sanitary napkins, panty liners, incontinence products. However, articles such as sweat-absorbent underarm pads, nursing pads, collar inserts, absorbent wound dressings and any other articles used to absorb body fluids or body exudates can also benefit from the present invention.

The term 'disposable' is used herein to describe absorbent articles that are not intended to be launched or otherwise restored or reused as absorbent articles (i.e., they are intended to be discarded after a single use and, preferably to be recycled, composted or otherwise disposed of in an environmentally compatible manner).

The term "use", as used herein, refers to the period of time that starts when the absorbent article is actually put in contact with the anatomy of the user.

In a preferred embodiment of the invention the color printed laminated structure consists of two layers, i.e., the first and second layers, as described herein after. In such executions the term "inner surface" of respectively the first and second layer of the laminated structure, refers to the surface of the first layer facing the second layer and to the surface of the second layer facing the first layer, the "outer surface" of respectively the first and second layer is accordingly respectively the opposite surface of each layer. In other words, in the preferred embodiment wherein the laminated structure consists of the first and second layers, the outer surfaces of the first and second layers form the outer surfaces of the laminated structure.

Color Printed Laminated Structure

The present invention relates to a color printed liquid permeable (fibrous) laminated structure primarily intended for acquiring, diffusing and absorbing fluids, typically body fluids. The structure comprises at least two layers, a first layer that is color printed on at least one of its surfaces and a second layer, the so-called fibrous web. In preferred embodiment herein the color printed fibrous laminated structure consists of only the first and second layers as described herein.

In a preferred embodiment, the laminated structures of the present invention are incorporated into absorbent articles, intended for absorption of body fluids. Preferably it is used as topsheet, more preferably as a secondary topsheet underlying a primary topsheet. Such a secondary topsheet is intended to acquire and diffuse body fluids through the primary topsheet towards the absorbent core. Alternatively the color laminated structures according to the present invention can constitute integrally the absorbent core of a disposable absorbent article, or they can be comprised therein as part of the absorbent core.

It has surprisingly been found that by color printing a first liquid permeable layer prior laminating it to a second liquid permeable layer, preferably a (dry laid) fibrous web and stabilizing the resulting structure per bonding means, preferably a latex binder, a color stable printed liquid permeable laminated structure is provided that retains its acquisition, diffusion and absorption properties towards body fluids.

Advantageously the color printed laminated structure according to the present invention has improved color bleeding resistance that reduces the transfer of printed ink to other surfaces/layers and improved color rub-off resistance, while retaining desired physical characteristics of the laminated structure as a whole, like softness, drapability, thickness, wettability and fluid acquisition speed.

In a preferred embodiment herein the color printed laminated structures according to the present invention meet at least one of the parametric features specified herein after and preferably all of them. Indeed the color printed laminated structures according to the present invention typically have a color fastness to water when measured according to ISO 105-E01 of at least 3, preferably of 4 or more, typically a color fastness to rubbing when measured according to ISO 105-X12 in dry condition of at least 3, preferably 4 or more and in wet condition of at least 2, preferably of 3 or more, and typically a color fastness to perspiration when measured according to ISO 105-E04 of at least 3 and preferably of 4 or more (for independently both alkaline solution and acid solution). These test methods are standard ones as described in respective ISO test (International Organization for Standardization). The measures are performed on a scale of 1 (the worst rating) to 5 (the best rating) as provided in these test methods.

Highly preferred herein the color printed laminated structure is a dry laid laminated structure described in more details herein after.

The dry laid manufacturing process used herein comprises a web formation and layering step and a web bonding and stabilizing step; in dry laying processes in fact the fibres, that can be of any type, e.g. cellulosic, synthetic, or any combination thereof, are formed or condensed into a web. Further components that are not in fibre form can also be incorporated in the fibrous web, e.g. a particulate material like an odour controlling agent and/or superabsorbent material as desired. The resulting web lacks integrity after formation, and must therefore be stabilized. Different techniques for bonding and stabilizing a dry formed web might be used herein including mechanical, thermal and chemical bonding processes. Bonding a web structure by means of a chemical is one of the most common methods of bonding in the non-woven industry, and consists in the application of a chemical binder to the web and in the curing of the binder, preferably latex binder. Advantageously latex is cheap, versatile, easy to apply, and very effective as a binder. Several methods might be used to apply the latex binder to the fibrous web, while spray bonding and print bonding are particularly preferred for fibrous webs intended to be used in absorbent articles.

First Layer of the Color Printed Laminated Structure

The first layer is liquid permeable (in other words fluid pervious) permitting body fluids (e.g., menses and/or urine) to readily penetrate through its thickness.

A suitable first layer can be manufactured from a wide range of materials such as woven, non-woven materials, knits, and films. Suitable woven and non-woven materials can be comprised of natural fibers (e.g., wood or cotton fibers), synthetic fibers (e.g. polymeric fibers such as polyester, polyolefin fibers such as polypropylene or polyethylene fibers), a combination of natural and synthetic fibers or bi-/multi-component fibers.

Examples of commonly employed polyolefins are polypropylene and polyethylene, including low density, high density, and linear low density polyethylene. It should be appreciated, however, that the present invention is not limited to these types of polyolefins, and embraces all types of polymers, copolymers, and natural fibers. In woven material applications, these materials can be made into continuous fibers, which are in turn woven into a fabric. In nonwoven applications, the fibers may be long, generally continuous fibers, such as spunbond and meltblown fibers, or they may be shorter staple length fibers, such as are commonly used in carded webs. Such polymers or copolymers may be extruded, cast, or blown into films for subsequent use according to the present invention.

The fibers used in the first layer of the laminated structure herein can be "straight" fibers in that they have the same general polymer or copolymer composition throughout. The fibers may also be multipolymer or multicomponent fibers, such as bicomponent fibers in which at least one component is a polyolefin, such as a polyethylene sheath and a polypropylene core fiber, or a polyethylene sheath and a polyester core fiber. In addition to sheath/core fiber configurations, other examples of suitable fiber cross-sections are side-by-side, sea-in-islands, and eccentric fiber configurations. Furthermore, fibers with non-circular cross-sections such as "Y" and "X" shapes may be used.

The fibers and/or webs may have other components and/or treatments. For example, adhesives, waxes, flow modifiers, processing aids and other additives may be used during the formation of the fibers and webs. In addition, pigments may be added to the fibers to change their color and other additives may be incorporated into the compositions to make the fibers and/or webs elastic. Lastly, blends of fibers, as well as straight and bicomponent fibers, may be combined to form nonwoven webs suitable for use as the first layer of the laminated structure of the present invention.

When forming a nonwoven, such as a nonwoven polyolefin fibrous web, the fiber size and basis weight of the material can be varied according to the particular end use. In personal care product, typical fiber sizes will range from between about 0.1 to about 10 denier, and basis weights will range from between about 10 grams per square meter to about 105 grams per square meter. For other applications, both the fiber size and the basis weight can be adjusted.

Examples of suitable first layer for use herein are spunbonded polypropylene nonwoven, 17 gsqm, commercially available from BBA (full name) under code 1WH05-01-17B and/or spunbonded polyethylene nonwoven, 17 gsqm, commercially available from BBA Lynotec under name T27AXC.

It is an essential feature of the invention that the first layer is color printed on at least one of its surface. Color printing process is described herein below in more details.

The inherent color of the first layer material might affect the color printing especially of lighter tints color printing. It will be appreciated that color printing are more distinct against a soft (yellowish) white, whilst process colors reproduce most accurately on neutral white material. The brightness of the first layer material may be altered, to adjust the contrast or brilliance of the color printing. Color reproduction may be affected if artificial brighteners (e.g., fluorescent additives) are incorporated in the first layer material, since most artificial brighteners are not neutral in color but, rather, have excess blue reflectance. Although per se the first layer might be colored (i.e., might have another color than white) it is highly desirable that the first layer per se is not colored, i.e. is white, prior undergoing color printing as described herein after.

Whatever surface of the first layer that is color printed, the resulting colored print is visible not only on the surface printed but also through the thickness of the first layer on its opposite surface (i.e. surface of the first layer being opposite to the one printed). Thus in the embodiments herein wherein the color printing occurs on the first layer on at least the surface thereof directly adjacent to the second layer in the laminated structure, prior laminating the first layer to the second layer, the color print is visible through the thickness of the first layer on its opposite surface (which, in the preferred structure herein consisting of only two layer, i.e., the first and second layers, corresponds to the outer surface of the laminated structure). This is achieved per the properties of the first layer, for example nonwoven, such as fibers transparency, and/or open area percent within the first layer and/or low basis weight. It is common practice to those skilled in the art to vary such parameters to obtain the desired relative transparency. Alternatively transparency might be obtained per heat application and/or pressure, for example per application of an embossment pattern.

The first layer is color printed on at least one area of at least one of its surfaces. At least one surface of the first layer is color printed following any desired image. Per 'image' it is understood herein the overall picture printed onto at least one surface of the layer. The image might cover only a limited area of the surface of the layer, typically in the center (so as for example to identify/visualize the body fluid discharge area when used into a disposable article for feminine protection), to the whole surface of the layer. The image can be a plain color printing or can be made of various indicia composing the image. Accordingly the image includes any form of color printing from uniform printing of only one color to multiple indicia of multiple colors. Indeed, the image and indicia may be of various colors and/or tones, with different distributions and densities depending on the requirements of use. The image and indicia might have any size or shape. The image/indicia may be regular or irregular in shape. Suitable image/indicia include, but are not limited to, any type of designs, marks, figures, identification codes, words, patterns, and the like. Example of image/indicia include, but are not limited to, triangles, tetragons, pentagons, hexagons, circles, ellipses, crescent-shapes, teardrops, ob-round shapes or a mixture thereof. In the case of a plurality of indicia forming the image, the color printed indicia can be the same or different (color, shape and/or form), being irregularly or regularly spaced on the surface of the layer to which they are printed.

Figure 5:
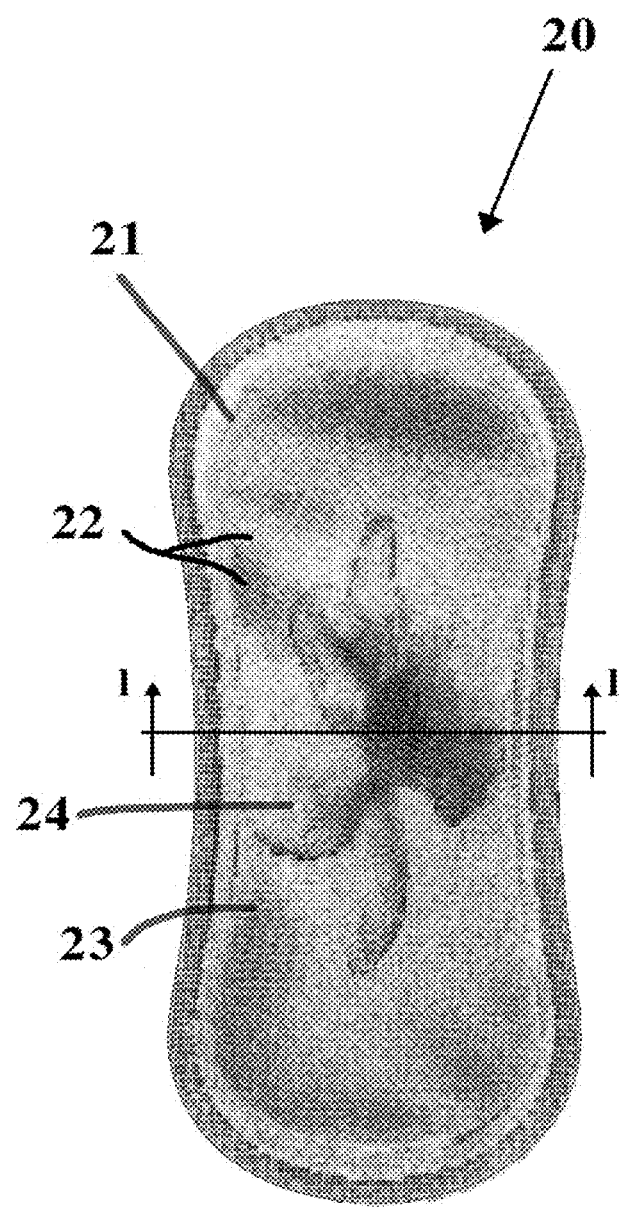
FIG. 5 is top view of a feminine protection absorbent article according to the present invention.
Figure 6:
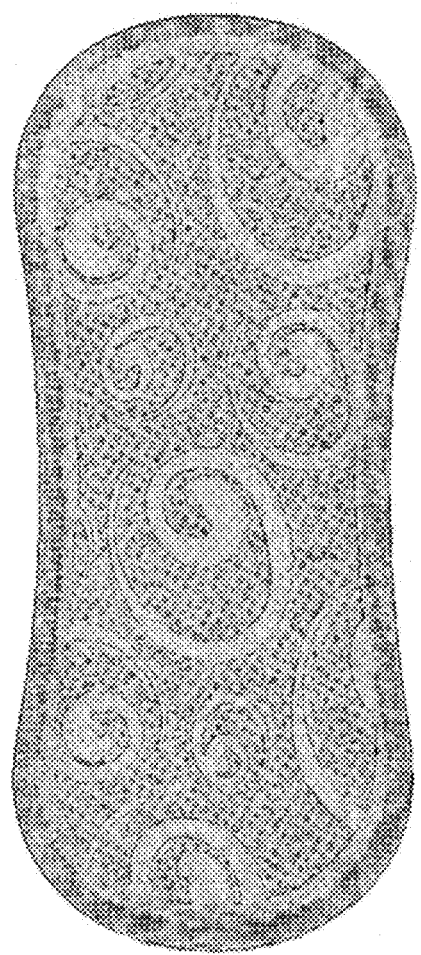
FIG. 6 is an alternative top view of a feminine protection absorbent article according to the present invention.

Examples of color printed images in absorbent articles are shown in FIGS. 5 and 6.

The colored image printed onto at least one surface of the first layer might be of any color, including only one color or combination thereof. It will be appreciated that the color choice may have a psychological effect since, for example, red would be an "angry" color whilst blue would be a calming color or green a relaxing color. In a particularly preferred embodiment according to the present invention, the color is selected within a range of colors from yellow to blue (440 to 580 nanometers), i.e., colors being complementary to the colors of menstruation (dominantly red) and hence are able to absorb the red wavelengths of the light that are the ones reflected by a dominantly red color. Advantageously by color printing a layer with such a color or combination thereof, the visibility of menstrual blood stains absorbed onto such a layer is reduced. In other words, the stains seem to be smaller and less vivid per visual inspection when using color printed laminated structures according to the invention printed with colors ranging from yellow to blue (440 nm to 580 nm) in absorbent articles in contrast to color printed laminated structures printed with colors ranging from violet to orange. Considering that blood has not only one tonality, but a series of hues going from violet/magenta to orange, preferred colors used herein range from yellow to blue in order to provide enhanced blood masking effect for all those tonalities.

In an alternative embodiment, if the first layer is pre-colored, the colored image may be applied in white ink. This gives a reversed, but sharper, impression of printed image.

The Second Layer of the Color Printed Laminated Structure

The second layer of the color printed laminated structure is a fibrous web.

Fibrous web for use herein include spunlaced, wet laid web and dry laid fibrous web. Dry laid fibrous web are preferred herein and described in more details herein after.

Dry laying and, more specifically, air laying processes are widely used to produce webs from dry fibres. Particularly, dry laying refers to the formation of carded webs, i.e., webs in which the fibres are oriented (carded) in a given direction, whereas the air laying process refers to the formation of webs with a completely random fibre orientation; the properties of such air laid webs are therefore somewhat isotropic. The fibrous webs produced by dry laying processes are soft, flexible and porous.

The fibrous structures of the present invention can be made using conventional equipment designed for dry laying processes, and although the invention is described hereinbelow with particular reference to air laid structures, it should be understood that other dry laying processes, e.g. carding, are also applicable.

The dry laid fibrous web used in the laminated structure of the present invention is soft and yet strong and absorbent. It can be desirable for preferred dry laid fibrous webs of this type to have relatively low bulk. A reduction in bulk, which means a reduction in volume the fibrous web is occupying, without sacrificing significantly other desired properties is important from the standpoint of manufacturing, storage and packaging. Hence, for dry laid fibrous web (second layer) used according to the present invention the basis weight can range from about 5 $g/m^2$ to 600 $g/m^2$, preferably from about 10 $g/m^2$ to 300 $g/m^2$, more preferably from about 20 $g/m^2$ to 100 $g/m^2$ and most preferably from about 40 $g/m^2$ to 70 $g/m^2$. Advantageously the strength of the laminated structure according to the present invention is provided per the first layer for example nonwoven, which acts as a carrier, giving the main strength to the resulting laminated structure. When the basis weight exceeds the upper limit, the product may be too stiff and therefore not useful for most applications.

The air laid fibrous web herein comprises randomly distributed fibres. Any of a variety of fibres, including a blend or admixture, can be used in the fibrous web herein. The fibres may be cellulosic, modified cellulosic, or synthetic, and include such fibres as wood pulp, rayon, cotton, cellulose acetate, polyester, polyethylene, polypropylene, nylon, and the like. A fibrous web comprising cellulosic fibres such as wood pulp fibres is particularly useful for use as an absorbent structure or topsheet in feminine protection absorbent articles as sanitary napkins or panty liners because the cellulose is liquid absorbent, therefore enhances the overall absorbency of the laminated structure as well as creates a network that contributes to the strength of the overall structure and retains particles that might be present like for example polyethylene powder. Blend of cellulosic and synthetic fibres might also be used, typically blend comprising about 65% to 95% by weight of cellulosic fibres, and corresponding remaining percent of synthetic fibres and more preferably up to about 20% by weight of the synthetic fibres. The synthetic fibres, which can be provided in any length including staple length, can improve the strength of the structure. They can also be treated to make them hydrophilic, in order not to decrease the fluid handling properties of the fibrous web.

The Bonding Means

The laminated structure according to the present invention is stabilized per bonding means.

Suitable bonding means for use herein are any means able to bind the fibers of the laminated structure and hence stabilize the laminated structure according to the present invention. Suitable bonding means for use herein include any conventional binder known to those skilled in the art including but not limited to glue, adhesive, latex binder, heat sealable material like for example thermoplastic polymeric material Highly preferred for use herein are latex binders, alone or in combination with other bonding means, preferably thermoplastic polymeric material.

For example latex binder is applied as an aqueous emulsion or dispersion, which typically contains about 2% to 20% solids, preferably 2% to 10% solids, and such materials are readily available from several manufacturers. Because the latex emulsions are water miscible, they may be further diluted, if desired, before being applied to at least one layer of the laminated structure, preferably the outer layers. Also, these latex compositions are thermosetting, and in order to effect cross-linking, they contain a small amount of a suitable cross-linking agent which are well known chemical agents for this purpose, such as N-methylolacrylamide. Any type of latex binder known in the art, which is suitable for stabilizing (fibrous) laminated structures can be used herein, provided that it preferably does not generate detectable odours, especially after curing, since this could be unpleasant for a user. Latices available are classified by chemical family, and those particularly useful include vinyl acetate and acrylic ester copolymers, ethylene vinyl acetate copolymers, styrene butadiene carboxylate copolymers, and polyacrylonitriles, and are sold, for example, under the trade names of Airbond, Airflex and Vinac of Air Products, Inc., Hycar and Geon of Goodrich Chemical Co., and Fulatex of H. B. Fuller Company. The amount of latex binder used cannot be so high as to substantially impair the fluid handling properties of the fibres, or as to impart a stiffness to the structure to render it impractical. Typically the latex binder may range from about 2% to 30% by weight of the laminated structure, and preferably from about 4% to 8% by weight.

The latex binder is applied on at least one of the outer surface of the laminated structure after having color printed the first layer and laminated it with fibres to form the dry laid web, thereby stabilizing the whole structure and especially the fibres within the dry laid web, and hence preventing dust going out of the resulting laminated structure. Advantageously the latex binder also stabilizes the color printed image printed on one of the surface of the first layer of the laminated structure, especially when the latex binder is applied on (the outer surface of) the first layer.

Preferably the latex binder is applied on both outer surfaces of the laminated structure, i.e. in the preferred embodiment herein the outer surface of the first layer and outer surface of the second layer, fibrous web, for optimum integrity/stability of the whole structure and optimum reduction of color-bleeding and rub-off.

Figure 2:
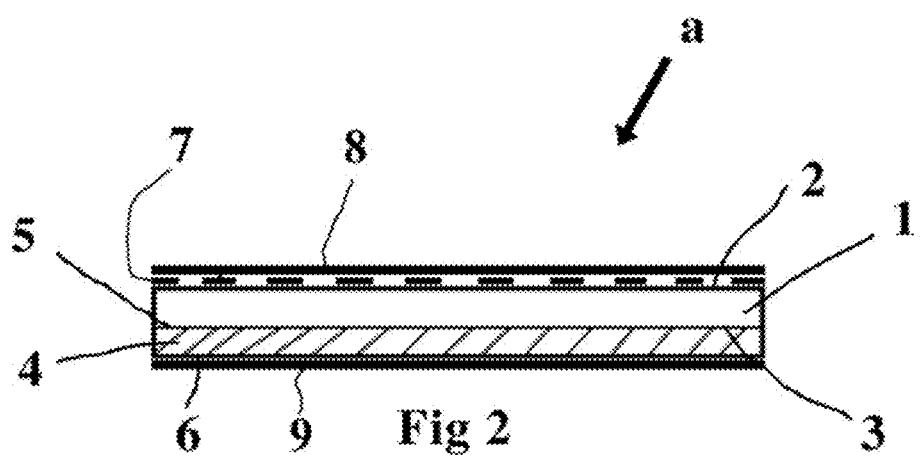
FIG. 2 is an enlarged cross-sectional view of a color printed laminated structure according to the present invention.
Figure 3:
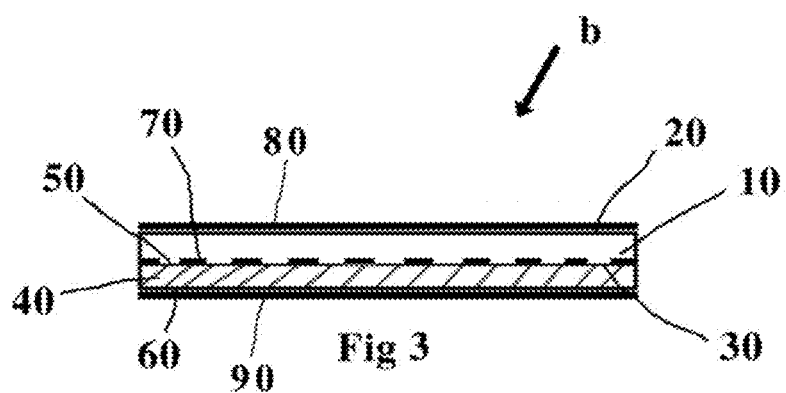
FIG. 3 is an enlarged cross-sectional view of an alternative embodiment of a color printed laminated structure according to the present invention.

This later execution is illustrated in FIGS. 2 and 3, where both the outer surface (2, 20) of the first layer (1, 10) and the outer surface (6, 60) of the second layer (4, 40) of the color printed laminated structure (a, b) bear a latex coating, indicated in the drawing by lines (8, 9, 80, 90). The latex coating typically penetrates or impregnates the structure to some degree and partially coats most of the fibres. The penetration might be controlled as desired so as not to impair the characteristics of the laminated structure. Indeed the depth of penetration of the latex into the fibrous web (second layer) and/or first layer can be controlled by the vacuum applied by means of the suction boxes positioned in correspondence with the dispensing means dispensing the latex binder, and by the choice of the amount to be applied.

In another embodiment of the present invention the bonding means used herein is a thermoplastic polymeric material, alone or in combination with other bonding means, preferably latex binder. Optionally but highly preferred the fibrous web, especially dry laid web, might comprise a thermoplastic polymeric material in finely divided form, preferably in particle or powder form, beside the latex binder. Its distribution among the fibres of the dry laid web helps to bind the fibres upon thermal treatment. The subsequent thermal treatment melts the thermoplastic polymeric material and therefore creates a framework of discrete bonding points within the web, i.e. among the fibres where the thermoplastic polymeric material in finely divided form has been distributed. The use of thermoplastic polymeric material in finely divided form can advantageously be combined with latex bonding, e.g. the thermoplastic powder performs the bonding preferably of the inner portion of the dry laid web, while the application of a latex binder stabilizes the outer surfaces of the dry laid web. Typically the thermoplastic polymeric material may range from about 1% to 70% by weight of the total weight of the laminated structure, and preferably from about 10% to 60% by weight.

The (dry laid) fibrous web used according to the present invention might comprise a particulate material distributed in the web that is typically capable of performing absorption of aqueous fluids and/or control of the odours, e.g., those odours associated with the absorbed fluids. Preferably the particulate material comprises an absorbent gelling material and/or an odour control means, both in particle form.

The color printed laminated structures according to the present invention are illustrated in FIGS. 2 and 3. FIG. 2 shows a color printed laminated structure (a) with a first layer (1) made of non-woven and a second layer (4) being an air laid fibrous web, the first layer (1) having an outer surface (2) and an inner surface (3), the outer surface (2) being color printed, as indicated in the drawing per dotted line (7), the second layer (4) having an outer surface (6) and an inner surface (5), the structure being stabilized per latex coating on both the outer surface (2) of the first layer (1) and the outer surface (6) of the second layer (4), indicated in the drawing by respectively lines (8,9). FIG. 3 shows a color printed laminated structure (b) with a first layer (10) made of non-woven and a second layer (40) being an air laid fibrous web, the first layer (10) having an outer surface (20) and an inner surface (30), the inner surface (30) of the first layer (10) being color printed, as indicated in the drawing per dotted line (70), the second layer (40) having an outer surface (60) and an inner surface (50), the structure (b) being stabilized per latex coating on both the outer surface (20) of the first layer (10) and the outer surface (60) of the second layer (40), indicated in the drawing by lines (80, 90).

Examples of such color printed laminated structures illustrated in FIGS. 2 and 3 are laminates of two non-woven: The first layer can be made of a 17 g/sqm spunbonded polypropylene non-woven material referred to as product No. 1WH05-01-17B (or 'P-9') obtained from BBA, Linotec, color printed on one of its surfaces. The second layer can be a multi-bonded air laid non-woven material that is thermally bonded using polyethylene powder and latex bonding. In a preferred embodiment, this multi-bonded air laid non-woven material comprises about 60-70% cellulose fibres, 20-38% polyethylene powder and 2-10% of latex (40% of latex is preferably sprayed on the first layer and remaining 60% thereof is sprayed on the second layer of the laminated structure) and has a basis weight of 40-100 g/sqm. These two non-woven layers are preferably laminated together by deposition the multi-bonded air laid non-woven material on the spunbonded polypropylene non-woven material. The spunbonded material is used as a process aid or carrier web in the process of forming the laminated structure as described herein after. In alternative embodiments, the spunbonded polypropylene nonwoven material may have a greater or lower basis weight, or it may be replaced by an air laid tissue, a wet laid tissue or any of the materials described herein before.

Process of Manufacturing the Color Printed Laminated Structure

A suitable process for manufacturing a color printed laminated structure comprising two layers, a first layer and a second layer, which is a fibrous web, preferably a dry laid fibrous web, comprises at least the following steps:

(a)—providing the first layer and color printing it on at least one of its surfaces, (b)—then providing fibers onto the first layer to form the second layer, (c)—then applying bonding means, preferably latex binder, onto the outer surface of said second layer and curing and/or (d)—applying bonding means, preferably latex binder, onto the outer surface of said first layer and curing When both Steps (c) and (d) are carried out, this might be done in any sequence first (c) then (d) or first (d) then (c) or simultaneously, provided (a) and (b) are operated before (c) and (d).

The first layer might be color printed on its inner or outer surfaces or both of them. Preferably the first layer is color printed on its inner surface, the surface in face-to-face relation with (i.e., directly adjacent to) the second layer in the laminated structure. This construction is preferred as it further improves the abrasion resistance (color rub-off resistance) properties of the whole color printed laminated structure as well as further reduces occurrence of color bleeding, especially when used as a secondary topsheet in an absorbent article for feminine protection.

Advantageously the first layer is printed with a monocolor image or with a multi-color image. In this later embodiment where multi-color printing is desired tight registration is suitable. Tight registration refers to the precise alignment of the different colors comprising an image. Inherent difficulties in achieving tight registration include the distance between the color printing stations, the uniformity of the printing substrate, and the extensibility of the printing substrate.

Any printing process known in the art, for example, letterpress, lithography, gravure or silk screen are suitable for use herein. Suitable printing processes are, for example, described in U.S. Pat. No. 5,695,855. The colored image may be obtained by generating a halftone in any conventional way. Thus, a preferred printing process is half tone printing. As used herein, the term "halftone" means breaking up a continuous solid tone into a plurality of tiny individual indicia of varying sizes, shapes and/or tonal intensities (tonalities).

The inks used to form the colored image may be any ink known in the art such as those described in, for example, U.S. Pat. No. 5,695,855. The inks used should be safe for human use and should not have environmentally deleterious effects. The inks chosen should, of course, be suitable for the intended printing process. Thus, for example, letterpress and lithographic inks are fairly stiff and require long ink roller trains on the press, to obtain the required flow and film thickness for printing. In contrast, gravure and flexographic inks are very fluid and dry mainly by solvent evaporation. Inks for screen printing are paint-like in their consistency and drying characteristics. The inks used herein once applied onto the absorbent article and optionally stabilized thereon should be substantially insoluble in the fluids (e.g., menses and/or urine) to be absorbed by the absorbent article.

The present invention preferably utilizes flexographic printing to provide the proper balance of cost effective, high speed, high quality printing suitable for printing the first layer, preferably nonwoven fibrous web, while maintaining the tactile softness of the layer. Flexography is a printing technology, which uses flexible raised rubber or photopolymer plates to carry the image to a given substrate. The flexible plates carry a typically low-viscosity ink directly onto the substrate. The quality of flexographic print in recent years has rapidly advanced such that, for many end-uses, it is comparable to lithographic or gravure printing.

The types of plates that can be used with the process of the present invention include plates identified as DuPont Cyrel® HL, PQS, HOS, PLS, and LP, which may be obtained from E. I. DuPont de Nemours & Co., Inc., 1007 Market Street, Wilmington, Del. 19898; a plate identified as BASF Nyloflex®, which may be obtained from BASF, 1255 Broad Street, Clifton, N.J. 07015; and a plate identified as FlexLight® type FL-SKOR®, which may be obtained from W.R. Grace & Co., 5210 Phillip Lee Drive, Atlanta, Ga. 303336. Others include laser etched vulcanized rubber cylinders, such as those supplied by Luminite Products Corporation, 115 Rochester Street, Salamanca, N.Y. 14779, or by Flexo Express, 270 Rochester Street, Salamanca, N.Y. 14779; or rubber printing plates, such as those supplied by Fulflex, Incorporated, P.O. Box 4549, Middleton, R.I. 02804. The rubber plates and vulcanized cylinder could be natural rubber, EPDM, nitrites, or urethanes.

Although flexographic printing is preferred herein, other printing methods known to those skilled in the art might be used including screen printing, rotogravure printing, ink jet printing and the like.

In comparison to flexographic printing, screen printing equipment is relatively costly and cannot be run as fast as flexographic equipment.

Rotogravure printing uses an engraved print roll that increases the life of the print pattern and provides higher definition, but rotogravure entails higher cylinder costs and does not give consistent ink depositions on many non-woven substrates. However, rotogravure equipment can be used with water-based, solvent-based, and hot-melt, adhesive-based inks.

Ink jet printing equipment generally requires inks that have a very low viscosity, often in the range of 1 to 10 centipoises, in order to achieve appropriate processing and application. Water-based and adhesive-based inks can be brought into this range. An advantage of ink jet printing equipment is the relatively high speed at which it can be run. Although only one color can be used per jet, multiple jets can be used to provide multiple colors.

In printing processes, the ink would cover or print in a varying manner on bond points (i.e., those points where fibers cross and are bonded together), on the fibers themselves, and where the fibers merely cross, but are not bonded together. The varying ink printing or contrast is identified as a paler or more washed-out color, or even a change of color, due to the differences of surface characteristics between the bond points, fiber crossover regions, and the fibers themselves.

Suitable inks to be used herein include the so-called water-based ink and solvent-based ink.

A "solvent-based" ink does not use water as the mobile phase to carry various pigments, resin(s) or binder(s), and additives, such as wax. Typically, "solvent-based" inks use one or more of various organic solvents such as alcohols, esters, aliphatics, and aromatics to solubilize these components. Solvents that solubilize resins well are generally referred to as "active", while those that are not "active" are called "diluents". A "water-based" ink typically uses water predominantly as the mobile phase. Resins used with water-based inks typically are emulsions, and can be dispersions in some cases. Other solvents may be added to act as co-solvents or coalescing agents to help emulsions form a continuous film.

Solvent-based inks that typically use aliphatic hydrocarbons with common binder types, such as polyamide, shellac, rosin esters, nitro-cellulose, and styrene-maleic are suitable for use herein. Highly preferred solvent-based ink includes non-catalytic, block urethane resin, which have demonstrated superior durability over traditional flexographic binders, such as styrene-maleic, rosin-maleic, acrylic solutions.

Desired solvent blends include blends ranging in volume up to about 50% of various acetates such as ethyl acetate, N-propyl acetate, isopropyl acetate, isobutyl acetate, N-butyl acetate, and blends thereof; up to about 10% of various alcohols including ethyl alcohol, isopropyl alcohol, normal propyl alcohol, and blends thereof; and up to 75% glycol ethers including Ektasolve® EP (ethylene glycol monopropyl ether), EB (ethylene glycol monobutyl ether), DM (diethylene glycol monomethyl ether), DP (diethylene glycol monopropyl ether), and PM (propylene glycol monomethyl ether), which can be obtained from Eastman Chemical, P.O. Box 431, Kingsport, Tenn. 37662. Other suitable solvents can also be obtained from Union Carbide Chemicals, 39 Old Ridgebury Road, Danbury, Conn. 06817. A desired solvent blend is a blend of about 50% to about 75% glycol ether, about 25% to about 35% N-propyl acetate, and about 15% to about 25% N-butyl acetate. Other glycols can be used such as DOWANOL®, obtainable from Dow Chemical, Midland, Mich. 48640.

Suitable water-based inks for use herein include emulsions that are stabilized in water-ammonia, and may contain alcohols, glycols, or glycol ethers as co-solvents. Indeed, it is common practice to add organic solvents (7% maximum) to water-based inks: alcohols, e.g., propan-2-ol—to speed up drying and assist wetting, glycols, e.g., mono propylene glycol to slow down drying, glycol ethers, e.g., dipropylene glycol mono methyl ether to aid film formation. Such solvents are commodity chemicals, commercially available from various companies. Highly preferred water-based ink includes self-crosslinking acrylic copolymer emulsion, which has demonstrated superior durability over traditional non-crosslinking binders such as acrylic solutions and dispersion copolymers.

The water-based inks and solvent-based inks also include coloration in addition to the binders and solvents/water. Coloration is typically imparted by the use of inert pigments and dyes, collectively referred to as pigments for purposes of the present invention, which can be added in levels of about 0.25% to about 40% on a dry weight basis and preferably between 1 and 10%.

The most common pigments include azo dyes (for example, Solvent Yellow 14, Dispersed Yellow 23, and Metanil Yellow), anthraquinone dyes (for example, Solvent Red 111, Dispersed Violet 1, Solvent Blue 56, and Solvent Orange 3), xanthene dyes (Solvent Green 4, Acid Red 52, Basic Red 1, and Solvent Orange 63), azine dyes (for example, Jet Black), and the like.

Major organic pigments include dairylide yellow AAOT (for example, Pigment Yellow 14 CI #21095), dairylide yellow AAOA (for example, Pigment Yellow 12 CI #21090), Hansa Yellow, CI Pigment Yellow 74, Phthalocyanine Blue (for example, Pigment Blue 15), lithol red (for example, Pigment Red 52:1 CI #15860:1), toluidine red (for example, Pigment Red 22 CI #12315), dioxazine violet (for example, Pigment Violet 23 CI #51319), phthalocyanine green (for example, Pigment Green 7 CI #74260), phthalocyanine blue (for example, Pigment Blue 15 CI #74160), naphthoic acid red (for example, Pigment Red 48:2 CI #15865:2).

Inorganic pigments include titanium dioxide (for example, Pigment White 6 CI #77891), carbon black (for example, Pigment Black 7 CI #77266), iron oxides (for example, red, yellow, and brown), ferric oxide black (for example, Pigment Black 11 CI #77499), chromium oxide (for example, green), ferric ammonium ferrocyanide (for example, blue), and the like.

Besides the solvent and pigments, the inks preferably comprises a binder or mixtures thereof. The binder helps stabilizing the pigment onto the support to which it is applied to. Typically the pigment-to-binder ratios is typically from 1:20 to 1:2 and preferably ranges up to about 1:1.7.

Waxes are also included in the present invention to increase the slip and improve the rub-resistance of the inks of the printed polyolefin substrate. Common classifications of waxes include animal (for example, beeswax and lanolin), vegetable (for example, carnauba and candellilia), mineral (for example, paraffin and microcrystalline), and synthetic (for example, polyethylene, polyethylene glycol, and Teflon®). A recommended range is between about 0.5% to about 5% wax based on the total formula weight.

The printing provided can be single color or multiple-color depending upon the aesthetic needs. According to the present invention it is desirable to have an image in one or more colors or tonalities printed on at least one surface of the first layer such that it is visible to the wearer of an absorbent article comprising the laminated structure for example as a topsheet, preferably secondary topsheet. With feminine protection absorbent articles, for example, it is desirable to make the article as attractive and as fun as possible to wear in order to encourage woman especially teens to feel better and more relaxed during their periods.

The process of manufacturing color printed laminated structure according to the present invention will now be described by way of example, with reference to the accompanying drawings in which:

FIG. 1 is a simplified schematic illustration of a preferred embodiment for the manufacture of the dry laid fibrous laminated structure of the present invention. In accordance with this embodiment, the air forming system, indicated generally by the numeral 100, includes a distributor unit 101 disposed transversely above a continuous forming screen, the color printed first layer (e.g. color printed nonwoven) 102, mounted on rollers 103 and driven by a suitable motor (not shown), and vacuum means or suction box 104 is positioned beneath the screen. Upstream of the distributor unit 101 is a defibrator or feeder 105, such as a hammermill or Rando-Feeder, where bales, laps or the like (for example wood pulp provided per roll 106) are defiberized. The fibres may be cleaned and/or blended if necessary or desired depending largely on the type of fibres used, the blend of fibres used, and the end product sought. For example, wood pulp fibres can be blended with synthetic fibres and applied as a blend by a single distributor, or different fibres can be each conveyed by a different distributor to the first layer to form separate plies or layers.

The porous forming screen, the color printed first layer, e.g., nonwoven layer 102, is essentially coextensive with the distributors 101, and the vacuum belt or suction box 104 beneath the first layer draws the air stream downwardly and conveys the fibres to the surface of the first layer, thereby forming plies or a loose web, i.e. second layer of the laminated structure (air laid fibrous web). At this stage in the process, the resulting laminated structure exhibits little integrity, and the vacuum means 104 retains the loose, fibrous air laid web on the first layer 102. The air laid web has an outer surface that faces the distributor and an inner surface, opposite to the outer surface, that faces the forming first layer 102. At least one of the surfaces of the first layer 102 is color printed before undergoing the manufacturing of the dry laid fibrous laminated structure.

It should be understood that the system may be modified to control the composition and thickness of the end laminated structure. For example, the distributor unit can comprise a plurality of individual distributors, and although FIG. 1 shows schematically two distributors respectively at 101A and 101B, the number of distributors and particular arrangement can be altered or varied depending on such factors as machine speed, capacity, type of fibres, and end product desired.

In one embodiment herein the laminated structure formed on the first layer 102 might incorporate therein a particulate material. For example the particulate materials might be an absorbent gelling material or an odour control means, both in particle or powder form, or a mixture thereof. In such an embodiment a dosing unit or feed hopper (not shown), containing the particulate materials is for example positioned in between the distributor units, e.g., between distributors 101A and 101B.

In a preferred embodiment herein a thermoplastic polymeric material in finely divided form, preferably in powder form, is preferably added to the fibrous web. In the embodiment shown in FIG. 1 the thermoplastic polymeric material in powder form is supplied to the dosing unit 108 from the container 107, the dosing unit being located between the distributors 101A and 101B. In this manner, the thermoplastic polymeric materials in powder form are deposited between plies of fibres laid by each distributors 101A and 101B. That is, the thermoplastic polymeric materials are discharged from hopper 108 onto the moving layer of fibres laid down by distributor 101A, and the ply of fibres laid down by distributor 101B is laid over the thermoplastic polymeric material. It should be understood, however, that the plies are relatively porous, and therefore the thermoplastic polymeric material tend to distribute somewhat within adjacent plies. Therefore the resulting fibrous web comprises the thermoplastic polymeric material concentrated intermediate the thickness of the web, forming a region of the web in which the fibres constitute a lower percentage as compared to the thermoplastic polymeric material. Indeed it is preferred that the thermoplastic polymeric material is distributed within the thickness of the web, intermediate the outer and inner surfaces thereof. Alternatively the thermoplastic polymeric material (e.g., polyethylene) is mixed together to the fibers (typically cellulose fibres) in each dosing unit. For example the dosing unit 101a might contain 50% of cellulose and 50% of polyethylene, while the dosing units 108 and 101b might contain 75% cellulose and 25% polyethylene.

The resulting laminated structure 112 might require further stabilization. According to the embodiment of the present invention illustrated in FIG. 1 the laminated structure is bonded on one, or preferably both outer surfaces (outer surface of the first layer and/or outer surface of the second layer, i.e., air laid fibrous web) by means of the application of a latex composition. In the embodiment shown the laminated structure is preferably first passed between compression rollers 109, which may be heated, to densify the structure, but this step is optional. This densification step can enhance the penetration of the latex binder into the laminated structure, and the degree or percent of densification can vary depending on such factors as basis weight of the laminated structure, the desired degree of penetration of the latex binder into the laminated structure, and the end product sought.

After the (optional) compression rollers the laminated structure is transported to a suitable dispensing means 110, such as a spray nozzle, doctor blade, roller applicator, or the like, where a latex binder is applied to the outer surface of the fibrous web (air laid fibrous web) of the laminated structure. A vacuum applied by a suction box (not shown) is positioned beneath the dispensing means 110 and the laminated structure 112, and helps to draw the latex binder into the structure. The dispensing means or applicator 110 is essentially coextensive with the width of the fibrous air laid web, and preferably a substantially uniform coating is applied to the fibrous web surface. However, the latex binder may be applied as a non-uniform, random or pattern coating, and because the latex binder is water-based, it will diffuse throughout the fibrous web/laminated structure and function as a binder when cured.

The latex binder when cured imparts integrity to the fibrous web/laminated structure. The extent or degree of penetration of the latex binder into the web/laminated structure might be controlled by controlling the amount of latex applied and by controlling the vacuum applied to the web/laminated structure (the vacuum helps to draw the latex into the web/laminated structure). The amount of the latex binder is also kept to such an extent that it does not impair the absorbency and softness characteristics of the fibrous web and hence the resulting laminated structure.

The latex binder is usually applied as an aqueous emulsion, and can be a thermosetting plastic. In order to activate the latex, the latex emulsion might contain a suitable curing agent or cross-linking agent, and after the web is coated, the latex is cured to effect cross-linking. Most typically, curing is accomplished by passing the coated web/laminated structure through a hot air oven or through an air drier 111, and the temperature typically ranges from 100° C. to 260° C., but this depends upon the specific type of latex resin used, upon the curing agent or cross-linking agent, upon the amount of latex, the thickness of the web, the degree of vacuum, and the machine speed.

It is desirable to coat the outer surface of the first layer 102 of the resulting laminated structure 112 with latex binder as well, and this is readily accomplished by the dispensing means 118 as the laminated structure is conveyed via there under via pulleys 113 and 114. This step is desirable as beside stabilizing the laminated structure it also further stabilizes the color printing on the first layer, thereby further reducing color-bleeding in use conditions and color rub-off. Coating the outer surface of the first layer with latex is especially desired in the embodiment of the invention wherein the outer surface of the first layer is color printed. The second dispensing means 118 includes a suction box (not shown). This second latex coating is likewise cured by passing the laminated structure through a second oven 115 within about the same temperature range.

In the preferred embodiment herein wherein thermoplastic polymeric material has been added as shown in FIG. 1 per dosing unit 108, this material contributes to stabilizing the structure herein. Indeed bonds among the fibres are generated by the melting of the individual particles of thermoplastic polymeric material in powder form when in oven 111 and/or 115; as it melts, the thermoplastic polymeric material forms "bridges" connecting directly the fibres.

The overall surface area of the bond points represents a small fraction of the surface area of the fibres that are involved in the bonding, the characteristics of which thus remain almost unchanged.

The thermoplastic polymeric material in finely divided form, e.g. in form of powder has the purpose of bonding the particulate material and, at least partially, the fibres of the dry laid absorbent structure together by melting and forming discrete, spaced-apart bond points among the particles and the fibres. The thermoplastic polymeric material can also be used in other finely divided forms, e.g. in form of fibrils.

The melting is preferably conducted at temperatures so as to not affect the characteristics of the other constituents, i.e., fibres and optional particulate materials. These preferred characteristics can be achieved by a thermoplastic polymeric material in finely divided form having a melt flow index (M.F.I.), evaluated by the ASTM method D 1238-85 under conditions 190/2.16, of at least 25 g/10 min, preferably at least 40 g/10 min, and even more preferably at least 60 g/10 min.

If the fibres of the dry formed fibrous structure are short cellulose fibres, it is preferable to use a thermoplastic polymeric material composed of powder of high-density polyethylene with maximum dimensions of the particles of about 400 microns, characterized by a melt flow index of about 50 g/10 min, in a quantity between 12 g/m$^2$ and 90 g/m$^2$.

The resulting stabilized laminated structure 117 exiting from the last oven now exhibits sufficient integrity and can be rolled (e.g., as shown in FIG. 1 on a winding/roll slitting 116) or alternatively cut and packaged, etc.

The laminated structure made in accordance with the foregoing process is illustrated in FIG. 2 and FIG. 3. The first layer of the laminated structure comprises randomly distributed fibres, such as wood pulp fibres. In the preferred embodiment herein wherein the first layer comprises the thermoplastic polymeric material in powder form distributed randomly among the fibers of the first layer, this material performs the bonding of at least part of the fibres of the first layer of the laminated structure, i.e. those fibres that enter in contact with the thermoplastic polymeric material. Both outer surfaces (2, 6 and 20, 60) of the laminated structure (a, b) bear a latex coating, indicated in the drawing by lines 8, 9 and 80, 90. The latex penetrates or impregnates the outer surfaces of the structure to some degree and partially coats some of the fibres (not shown).

In an alternative embodiment of the present invention, not illustrated, the latex coating first is applied on the outer surface of the first layer of the structure and cured before being applied on the outer surface of the second layer, i.e. air laid fibrous web, or both steps are carried out simultaneously.

Absorbent Article

While the present invention will be described herein after in the context of sanitary napkins and panty liners, the invention might also be applicable as mentioned herein before for other protection than feminine protection, like adult incontinence protection or baby protection.

In a preferred embodiment herein the absorbent article according to the present invention comprises a topsheet, an underlying layer visible through the topsheet, an absorbent core and a backsheet. The underlying layer visible through the topsheet is directly adjacent to the topsheet, i.e. in face-to-face relation with the topsheet, typically located between the topsheet and the absorbent core. The underlying layer is made of the color printed laminated structure according to the present invention. Preferably the outer surface of the first layer of the laminated structure is facing the wearer (hence might also be called herein wearer facing surface) and the outer surface of the second layer of the laminated structure is facing the garment of the wearer (hence might also be called garment facing surface). In the preferred embodiment herein the underlying layer is the so-called secondary topsheet layer.

The Topsheet

The topsheet for use in the present invention also called herein after primary topsheet is formed from at least one primary top layer. In a preferred embodiment herein the primary topsheet is in face-to-face relation to an underlying layer, also called herein secondary topsheet.

The primary topsheet should be compliant, soft feeling, and non-irritating to the wearer's skin. The primary topsheet is fluid pervious, permitting fluids (e.g., menses and/or urine) to readily penetrate through its thickness. The underlying layer, typically the secondary topsheet, is visible through the primary topsheet so to allow recognition of color printed on the secondary topsheet per human eyes. The primary topsheet is typically provided with some regions, which are transparent as opposed to opaque. By 'opaque' it is referred herein to a material, which inhibits the passage of light, such that a color printed image located opposite the material can not be viewed by naked eyes. By 'transparent' it is referred to material through which light passes such that color printed image located opposite the transparent material can be viewed by the naked eye. Preferably herein the primary topsheet is provided with at least some regions which are transparent and most preferably the transparent areas represent at least 20%, preferably at least 50%, more preferably at least 90% and most preferably 100% of the whole topsheet (i.e. the topsheet is preferably completely made of transparent material). As a general rule a material will be considered to be transparent when it has a light transmission of greater than 50 percent, preferably greater than 80 and most preferably greater than 90.

A suitable primary topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and non woven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers.

Preferred primary topsheets for use in the present invention are selected from high loft nonwoven topsheets and apertured formed film topsheets. Apertured formed films are especially preferred for the primary topsheets because they are pervious to body exudates and yet non absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. Nos. 3,929,135; 4,324,246; 4,342,314; 4,463,045; and U.S. Pat. No. 5,006,394. Particularly preferred micro apertured formed film primary topsheets are disclosed in U.S. Pat. Nos. 4,609,518 and 4,629,643. A preferred primary topsheet for the present invention comprises the three-dimensional formed film described in one or more of the above patents and marketed on sanitary napkins by The Procter & Gamble Company of Cincinnati, Ohio as "DRI-WEAVE". WO 97/14388 also describes a suitable apertured primary topsheet.

Preferred primary topsheets have apertures being dimensioned to permit show-through (or visualisation) of the colored printed image on the secondary topsheet. The pattern of apertures might be regularly spaced or random.

A preferred regularly spaced first pattern of apertures comprises a macroscopically expanded pattern of irregularly shaped pentagonal apertures described in U.S. Pat. No. 4,463,045. The primary topsheet described in U.S. Pat. No. 4,463,045 is a three-dimensional formed film comprising an array of sub-patterns, each sub-pattern comprising four irregular pentagonal apertures forming an irregular hexagon. Another preferred primary top layer exhibits apertures arranged in an ordered or pseudo-random array. A suitable ordered array may be a regular square, rectangular, rhomboidal or hexagonal array, the apertures themselves being square or, alternatively, circular or slightly elliptical as described in U.S. Pat. No. 4,780,352. The interspacing between adjacent apertures may be about 1.4 mm Overall, the ratio between the surface occupied by the apertures and the whole surface of the primary top layer is typically within the range 10-50%, depending on the requirements of use and the strength characteristics of the materials used. Preferably, the open area is about 25%. It will of course be appreciated that the apertures may be arranged in an array other than a regular square, rectangular, rhomboidal or hexagonal array or other than in a pseudo-random array.

Suitable apertures may be made by a perforating or punching action. A suitable perforating station would constitute two counter-rotating rollers, the lower roller of which acts as a rotary support and has a generally smooth surface and the upper roller of which has teeth or projections arranged in the array corresponding to the first pattern. Feeding of the primary top layer through the perforation station causes the teeth or projections of the upper roller to penetrate the primary top layer, thereby perforating its structure, as described in U.S. Pat. No. 4,780,352.

Primary topsheet being made of transparent/translucent material, in contrast to white conventional topsheet are highly preferred herein. Advantageously the use of such transparent topsheet enhances the visibility of the colored laminated structure positioned beneath the so-called primary topsheet. Such transparent materials are typically available by simply reducing or even omitting white pigment conventionally used during manufacturing thereof, like titanium oxide. The topsheet can be completely transparent or can be provided only with regions of transparency. Such material although provided with inherent transparency can further comprise apertures.

An example of transparent topsheet is commercially available under code name Ris CPM-Clear from Tredegar—Terrehaute—Indiana.

Alternatively the primary topsheet material might be made of conventional material (white) and treated to render it transparent. Such treatment generally consists of applying thermal energy through a discontinuous heat bonding, sonic bonding or pressure embossing operation.

The primary topsheet typically extends across the whole of the absorbent structure and outside the area coextensive with the absorbent structure.

When referring to the primary topsheet, a multi layer apertured structure or a mono layer apertured structure are each contemplated.

Absorbent Core

Absorbent cores suitable for use in the present invention may be selected from any of the absorbent cores or core systems known in the art. As used herein, the term "absorbent core" refers to any material or multiple material layers whose primary function is to absorb, store and distribute fluid. In one embodiment herein the color printed laminated structure of the invention might also be used as part of the absorbent core or as the absorbent core in its entirety.

Backsheet

The backsheet primarily prevents the exudates absorbed and contained in the absorbent structure from wetting garments that contact the absorbent product such as underpants, pants, pyjamas and undergarments. The backsheet is preferably impervious to fluids (e.g. menses and/or urine) and is preferably manufactured from a thin plastic film, although other flexible liquid impervious materials can also be used.

The backsheet can comprise a woven or nonwoven material, polymeric films such as thermoplastic films of polyethylene or polypropylene, or composite materials such as a film-coated nonwoven material.

Preferably the backsheet of the absorbent article is moisture vapour permeable and thus comprises at least one gas permeable layer. Suitable gas permeable layers include two dimensional, planar micro- and macro-porous films, macroscopically expanded films, formed apertured films and monolithic films. The apertures in said layer may be of any configuration, but are preferably spherical or oblong and may also be of varying dimensions. The apertures preferably are evenly distributed across the entire surface of the layer. However layers having only certain regions of the surface having apertures are also envisioned.

A preferred sanitary napkin or panty liner of the present invention has a pair of conventional flaps or wings. If desired these flaps or wings might also comprise a color printed laminated structure according to the present invention.

The invention will now be further described, by way of example, with reference to the accompanying drawings, in which:

FIG. 5 illustrates a top plan view of a sanitary napkin 20 viewed per its wearer facing surface, said napkin 20 comprising one primary top layer 21 and a secondary topsheet layer 23 visible through the primarily topsheet layer 21. The secondary topsheet layer 23 is provided with color printed image 24 visible through the primary topsheet layer 21. The primary top layer 21 is a three-dimensional formed film exhibiting a macroscopically expanded three-dimensional pattern of irregularly shaped pentagonal apertures 22. In an alternative embodiment not shown such a sanitary napkin can be embossed, embossing points are obtained as described in U.S. Pat. No. 4,397,644 or WO98/27904.

An alternative sanitary napkin is illustrated in FIG. 6. The sanitary napkin in FIG. 6 differs from the sanitary napkin illustrated in FIG. 5 only in the image color printed per flexography printing on the first layer of the laminated structure forming the so-called secondary topsheet.

Referring to FIG. 5, it will be observed that the color printed image 24 is positioned, shaped and dimensioned to be visible through the primary topsheet, namely through the apertures thereof. In an alternative embodiment the primary topsheet material per se is fully transparent (apertured or not) (e.g., Ris CPM-Clear [X-27221] from Tredegar—Terrehaute—Indiana), the color printed image being visible through the entire surface of the primary topsheet.

Figure 4:
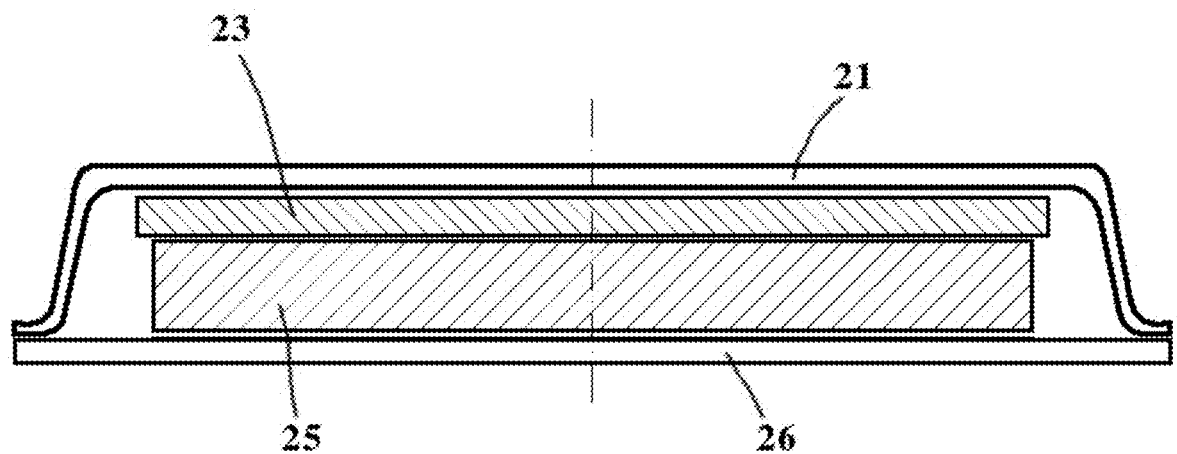
FIG. 4 is an enlarged cross-sectional view of a feminine protection absorbent article taken along line I-I of FIG. 5.

Referring now to FIG. 4 of the accompanying drawings, there is illustrated a cross sectional view of the sanitary napkin of FIG. 5. The sanitary napkin comprises

- as a primary topsheet 21, a white apertured polyethylene formed film having holes of 0.889 square millimeters, basis weight of 25 g/sqm and an open area of 80% (white CPM, code name X25602 commercially available from TREDEGAR, Terrehaute—Indiana)
- as a secondary topsheet 23, a color printed laminated structure (77 g/sqm) made of a 22% weight of spunbonded polypropylene nonwoven material having a basis weight of 17 g/sqm, referred to as product No. 1WH05-01-17B (or 'P-9') obtained from BBA, Linotec, color printed on its inner surface, together with a multibonded air laid nonwoven material made of 68% weight cellulose and 25% weight polyethylene powder of the total laminated structure basis weight, 4% latex per weight of total laminated structure applied on both side (2.5% on the multibonded air laid and 1.5% on the spunbonded polypropylene nonwoven). (cf. FIG. 3)
- a spiral layer of adhesive (H2545®, available from Ato Findley) (not shown in FIG. 4),
- a white absorbent tissue core 25 with 17% super absorbent fibers, polypropylene and polyethylene bi-component fibres and cellulose (code GH.150.1006, basis weight 150 gsm commercially available from Concert GmbH, Falkenhagen-Germany),
- a spiral layer of adhesive (H2545®, available from Ato Findley) (not shown in FIG. 4),
- as backsheet, a polyethylene micro embossed film 26, commercially available from Tredegar, under code XBF 616W
- stripes of panty fastening adhesive (LA203/TF1®, available from Savare) (not shown in FIG. 4), and release paper (not shown).

Advantageously the color printed laminated structure as described herein before as topsheet 23 (illustrated in FIG. 3) in the sanitary napkin (illustrated in FIG. 4) has a color fastness to water when measured according to ISO 105-E01 of 4, a color fastness to rubbing when measured according to ISO 105-X12 in dry condition of 4 and in wet condition of 3 and a color fastness to perspiration when measured according to ISO 105-E04 of 4 (both for alkaline solution and acid solution).

The invention claimed is:

1. A process for manufacturing a disposable absorbent article comprising a wearer-facing surface and a garment-facing surface, the method comprising the steps of:
   providing a first layer comprising a first surface and an opposing second surface, wherein the first layer comprises a film;
   color printing the first layer on at least one of the first surface or second surface, wherein the color printing comprises more than one color;
   providing a second layer comprising constituent fibers, wherein the second layer is a nonwoven and has a first surface and an opposing second surface;
   providing a topsheet, an absorbent core, and a backsheet, wherein the topsheet forms a portion of the wearer-facing surface and the backsheet forms a portion of the garment-facing surface; and
   placing the first layer and second layer between the topsheet and an absorbent core such that the color printing is visible through the wearer-facing surface.

2. The process of claim 1, wherein the constituent fibers are bi-component fibers which are configured in a side-by-side configuration.

3. The process of claim 1, wherein the second layer comprises a spunlace material.

4. The process of claim 1, wherein the second layer comprises an airlaid material.

5. The process of claim 1, further comprising the step of joining the first layer and the second layer.

6. The process of claim 5, wherein the step of joining the first layer and the second layer comprises a mechanical bonding process.

7. The process of claim 5, wherein the step of joining the first layer and the second layer comprises a thermal bonding process.

8. The process of claim 5, wherein the step of joining the first layer and the second layer comprises adhesive added to the first layer and the second layer.

9. A process for manufacturing a disposable absorbent article comprising a wearer-facing surface and a garment-facing surface, the method comprising the steps of:
   providing a first layer having a first surface and an opposing second surface, wherein the first layer is a film;
   color printing the first layer on at least one of the first surface or second surface;
   providing a second layer comprising constituent fibers, and wherein the second layer has a first surface and an opposing second surface;
   joining the first layer and the second layer together to form a laminate structure;

providing an absorbent core, and a backsheet, wherein the backsheet forms a portion of the garment-facing surface; and utilizing the laminate as a topsheet, such that the first layer forms a portion of the wearer-facing surface.

10. The process of claim 9, wherein the second layer comprises a spunlace material.

11. The process of claim 9, wherein the second layer comprises an airlaid material.

12. The process of claim 9, wherein the step of joining the first layer and the second layer comprises a mechanical bonding process.

13. The process of claim 9, wherein the step of joining the first layer and the second layer comprises a thermal bonding process.

14. The process of claim 9, wherein the step of color printing comprises more than one color.

15. The process of claim 9, wherein the color printing on the first layer has a color fastness of at least 3 according to ISO 105-E01.

16. The process of claim 9, wherein the color printing on the first layer has a color fastness to rubbing in a dry condition of at least 3 according to ISO 105-X12.

17. The process of claim 9, wherein the color printing on the first layer has a color fastness to rubbing in a wet condition of at least 2 according to ISO 105-X12.

18. The process of claim 9, wherein the color printing on the first layer has a color fastness to perspiration of at least 3 according to ISO 105-E04.

19. The process of claim 9, wherein the first layer is pre-colored.

20. The process of claim 9, wherein the laminated structure has a basis weight of between about 10 g/m^2 to about 300 g/m^2.

21. The process of claim 9, wherein the laminated structure has a basis weight of between about 20 g/m^2 to about 100 g/m^2.

22. The process of claim 9, wherein the laminated structure has a basis weight of between about 40 g/m^2 to about 70 g/m^2.

23. The process of claim 9, wherein the laminated structure comprises a blend of cellulosic and synthetic fibers.

24. The process of claim 23, wherein the laminated structure comprises between about 65 percent to about 95 percent cellulosic fibers and up to about 20 percent synthetic fibers.

25. The process of claim 23, wherein the synthetic fibers are staple length.

26. The process of claim 9, wherein the step of color printing the first layer utilizes a water-based ink.

27. The process of claim 9, wherein the step of color printing the first layer utilizes a solvent-based ink.

28. The process of claim 9, wherein the laminated structure is embossed.

29. The process of claim 9, wherein the color printing on the first layer is visible from the wearer-facing surface.

* * * * *